(12) United States Patent
Yoo et al.

(10) Patent No.: US 9,994,848 B2
(45) Date of Patent: Jun. 12, 2018

(54) PHARMACEUTICAL COMPOSITION FOR PREVENTING AND TEATING ENDOCRINE DISRUPTING CHEMICALS-INDUCED DISEASES AND TREATING METHOD USING THE SAME

(71) Applicant: Dong-A University Research Foundation for Industry-Academy Cooperation, Busan (KR)

(72) Inventors: Young Hyun Yoo, Busan (KR); Hye Young Kim, Gyeongsangnam-do (KR)

(73) Assignee: DONG-A UNIVERSITY RESEARCH FOUNDATION FOR INDUSTRY-ACADEMY COOPERATION, Busan (KR)

( * ) Notice: Subject to any disclaimer, the term of this patent is extended or adjusted under 35 U.S.C. 154(b) by 0 days. days.

(21) Appl. No.: 15/336,009

(22) Filed: Oct. 27, 2016

(65) Prior Publication Data

US 2018/0066250 A1    Mar. 8, 2018

(30) Foreign Application Priority Data

Sep. 8, 2016    (KR) .................. 10-2016-0115867

(51) Int. Cl.

| | | |
|---|---|---|
| *A61K 31/70* | (2006.01) | |
| *C07H 21/02* | (2006.01) | |
| *C07H 21/04* | (2006.01) | |
| *C12N 15/113* | (2010.01) | |
| *A61K 31/155* | (2006.01) | |
| *A61K 31/713* | (2006.01) | |
| *C12N 5/00* | (2006.01) | |

(52) U.S. Cl.
CPC .......... *C12N 15/113* (2013.01); *A61K 31/155* (2013.01); *A61K 31/713* (2013.01); *C12N 2310/14* (2013.01); *C12N 2320/31* (2013.01)

(58) Field of Classification Search
None
See application file for complete search history.

(56) References Cited

FOREIGN PATENT DOCUMENTS

| | | |
|---|---|---|
| JP | 2006-025647 A | 2/2006 |
| KR | 10-2007-0105685 A | 10/2007 |

OTHER PUBLICATIONS

"What is Endocrine Disruption?" United States Environmental Protection Agency http://www.epa.gov/endocrine-disruption/what-endocrine-disruption, down loaded Dec. 19, 2017, 3 pages.*
Ferrante MC. et al., "Polychlorinated biphenyls (PCB 101, PCB 153 and PCB 180) alter leptin signaling and lipid metabolism in differentiated 3T3-L1 adipocytes.", Toxicology and Applied Pharmacology, vol. 279(3), pp. 401-408, 2014.

* cited by examiner

*Primary Examiner* — Sean McGarry
(74) *Attorney, Agent, or Firm* — The PL Law Group, PLLC

(57) ABSTRACT

A pharmaceutical composition for preventing and treating endocrine disrupting chemicals-induced diseases and a treating method using the same. Since the composition has an effect of decreasing lipid accumulation caused by endocrine disrupting chemicals, for example, persistent organic pollutants (POPs) including polychlorinated biphenyl and the like and can improve insulin resistance caused by the POPs through reduction of insulin receptor substrate 1 (IR1), the composition can be helpfully used for treating diseases including obesity, insulin resistance, and the like caused by the endocrine disrupting chemicals. Further, according to the present disclosure, the composition has an effect of excreting the endocrine disrupting chemicals.

12 Claims, 34 Drawing Sheets

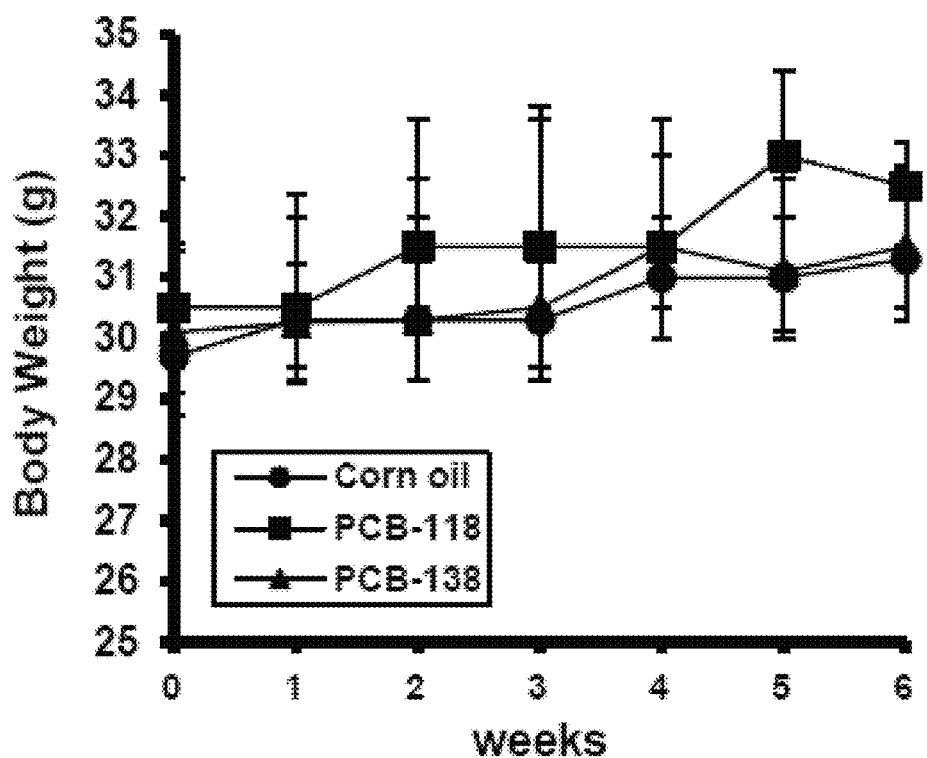

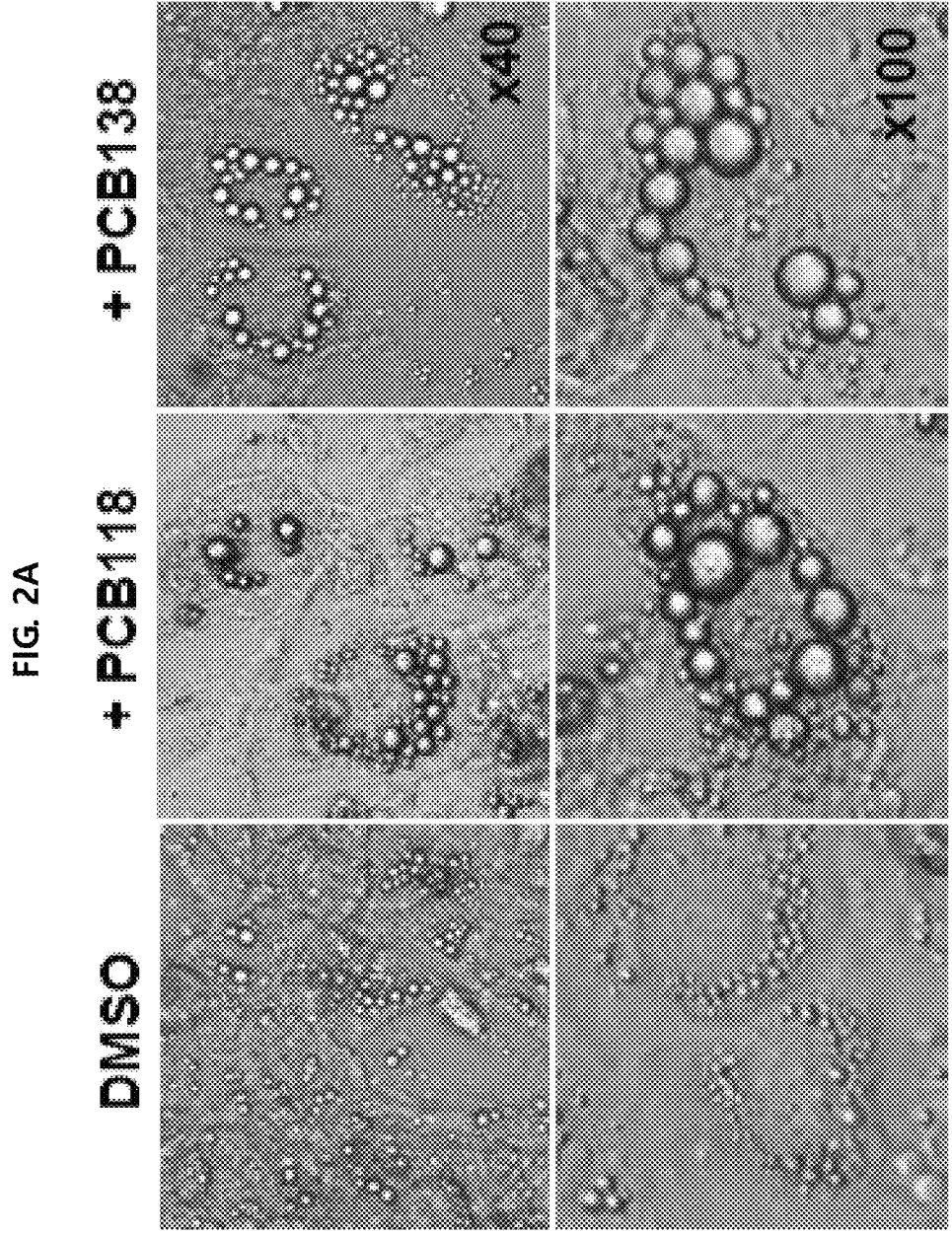

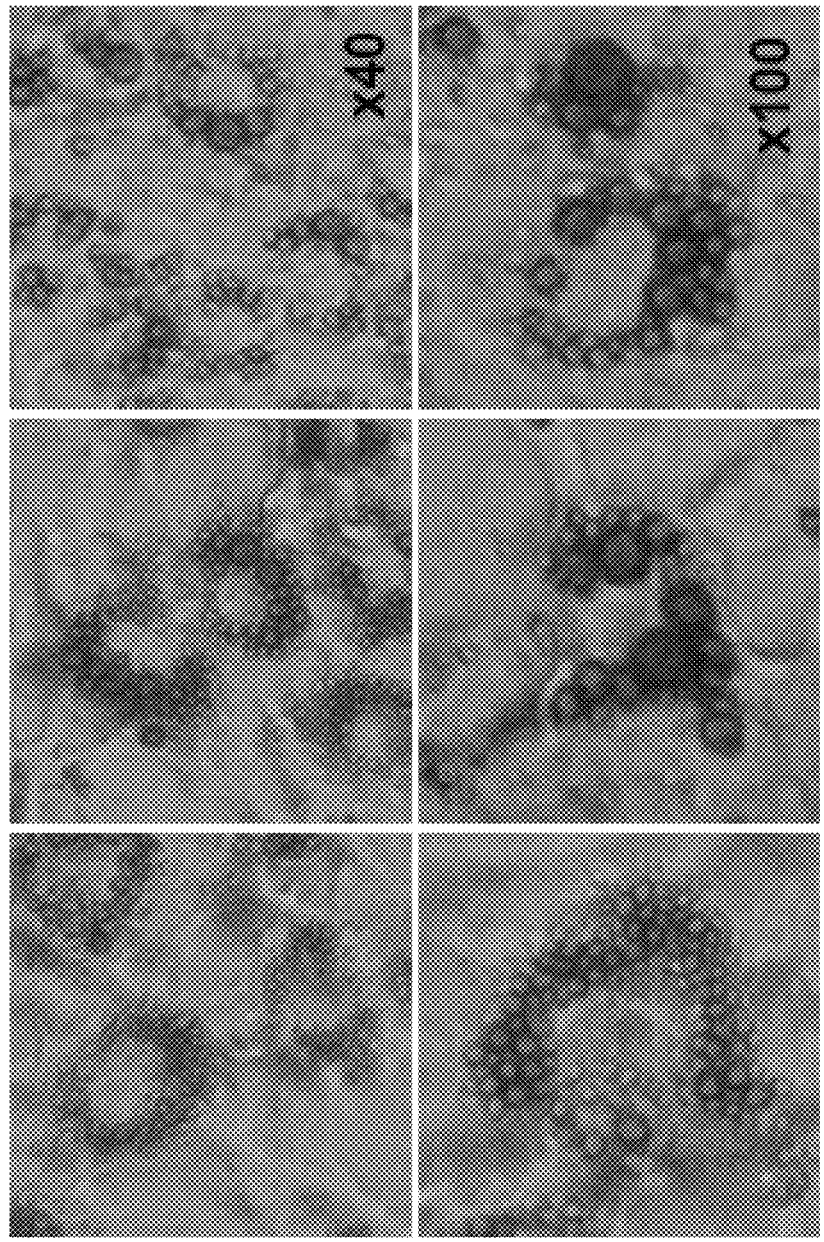

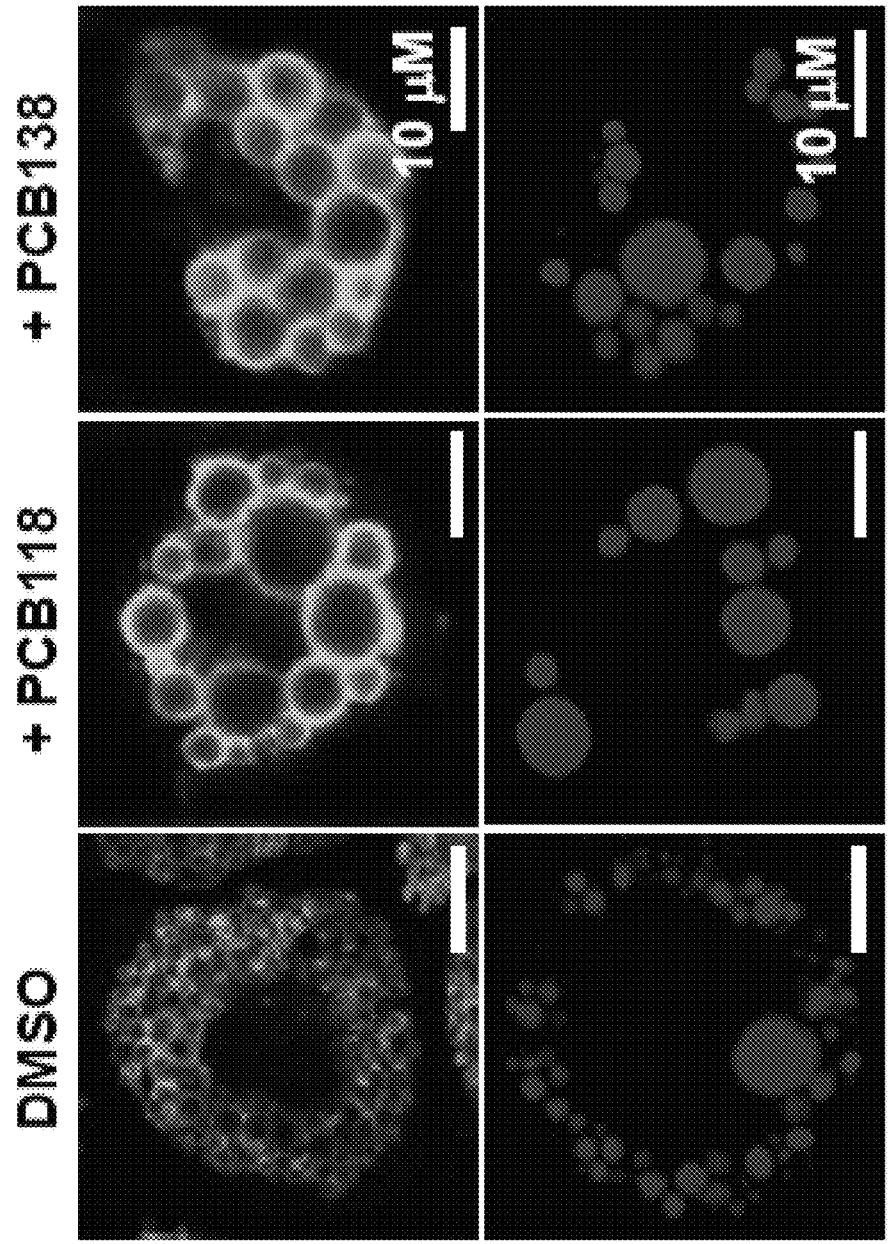

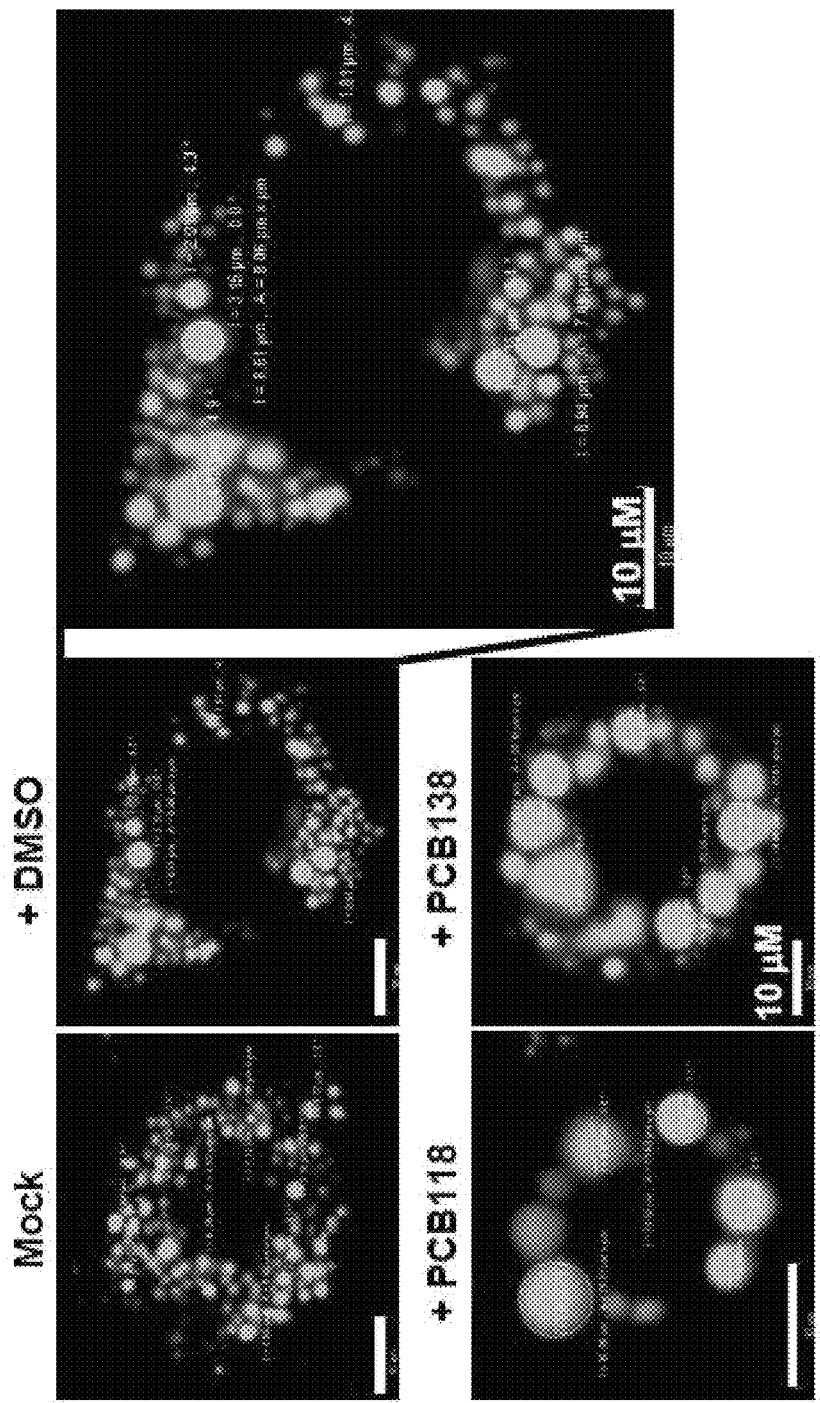

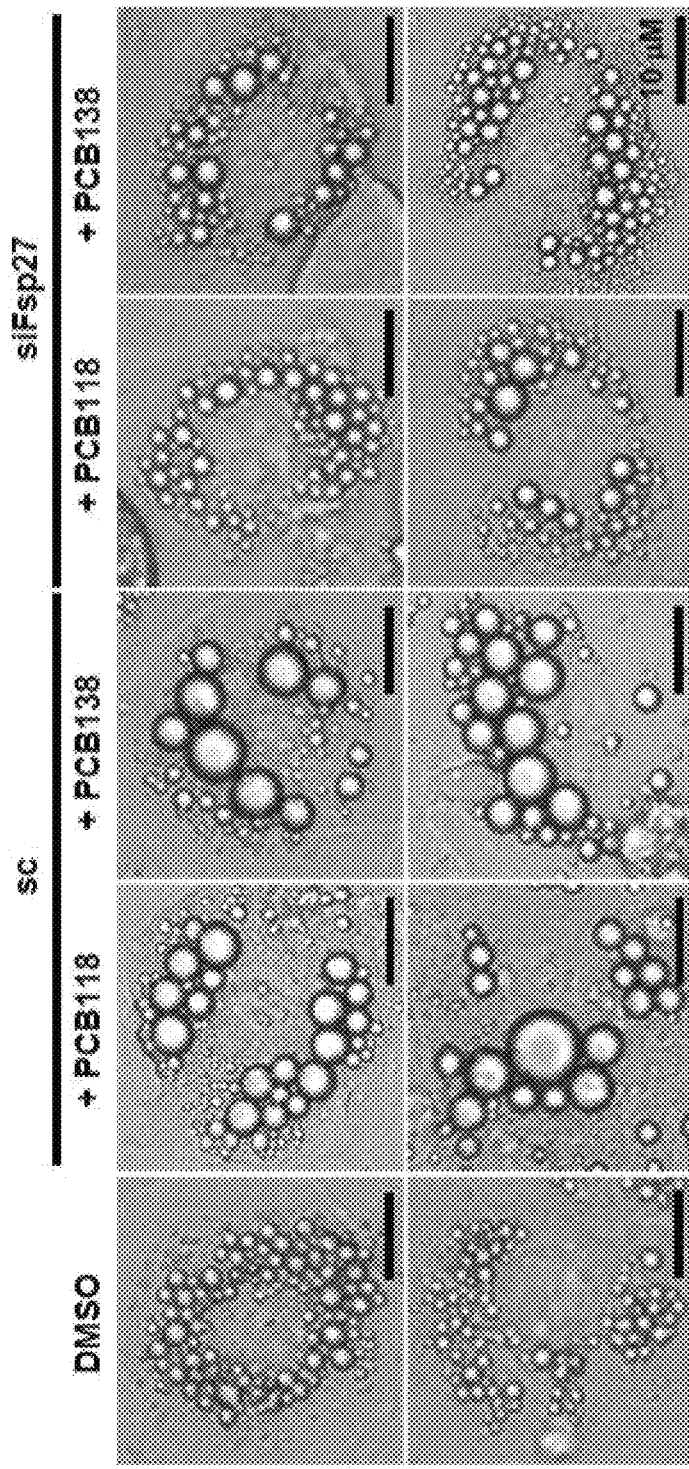

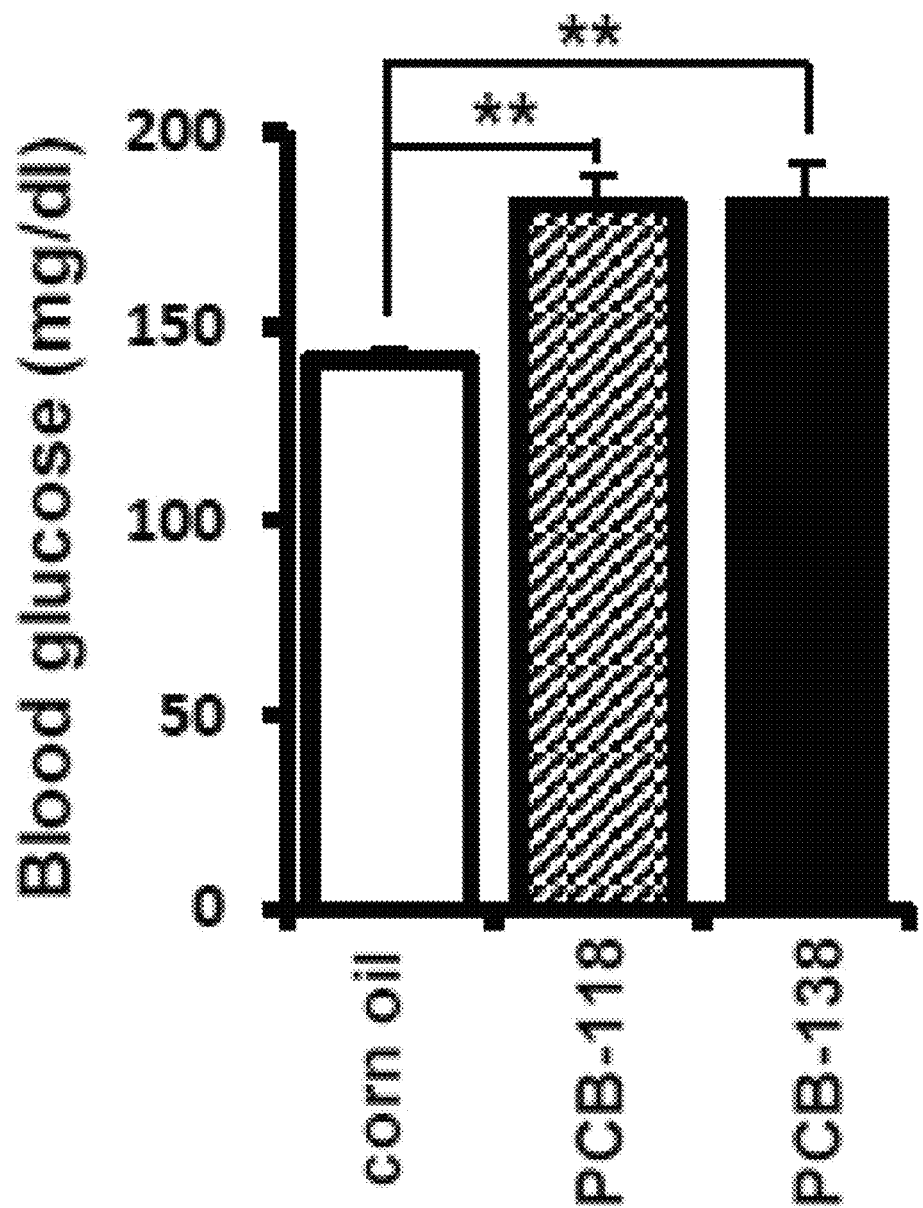

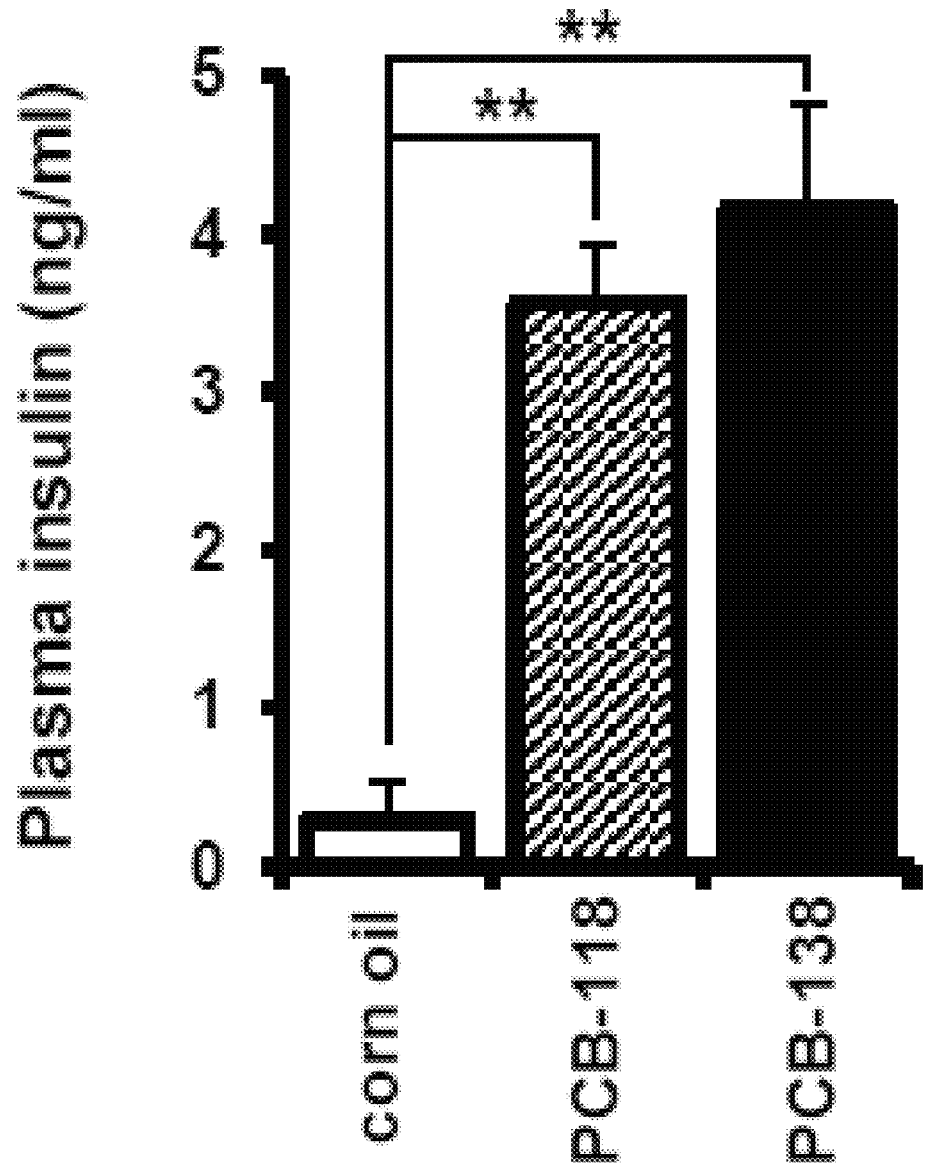

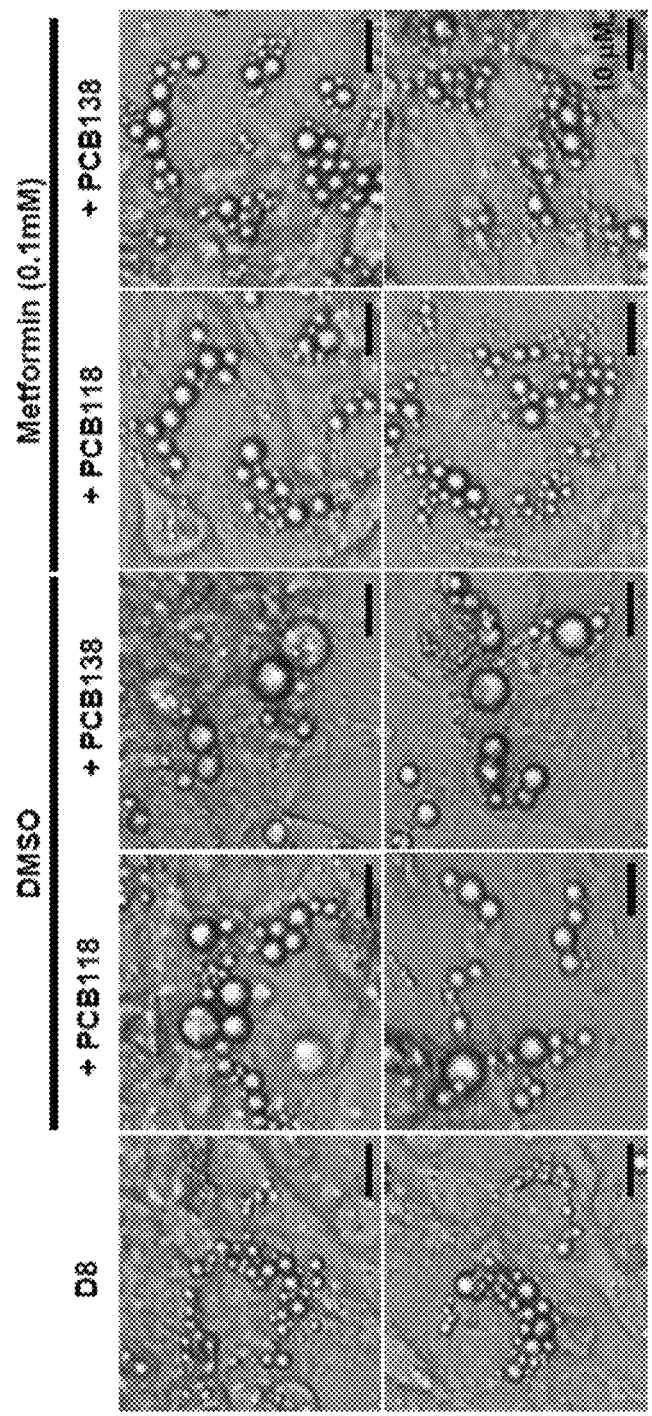

PHARMACEUTICAL COMPOSITION FOR PREVENTING AND TEATING ENDOCRINE DISRUPTING CHEMICALS-INDUCED DISEASES AND TREATING METHOD USING THE SAME

CROSS-REFERENCE TO RELATED APPLICATIONS

This application claims the priority of Korean Patent Application No. 10-2016-0115867 filed on Sep. 8, 2016, in the Korean Intellectual Property Office, the disclosure of which is incorporated herein by reference.

BACKGROUND

1. Technical Field

The present disclosure relates to a pharmaceutical composition for preventing and treating endocrine disrupting chemicals-induced diseases and a treating method using the same.

2. Description of the Related Art

Endocrine disrupting chemicals are defined as exogenous chemicals that may be involved in synthesis, storage, secretion, internal transport, binding, and metabolic processes of various bio-hormones associated with reproduction, generation, metabolism, immunity, and the like in all organisms having the endocrine system, as well as human bodies.

The endocrine disrupting chemicals are also called environmental hormones and exist as estrogenic chemicals which are synthesized by plants or microorganisms in the natural world in addition to synthetic chemicals.

In research reported in recent years, it has been verified that an increase in body weight has a statistically significant relevance with a concentration of chemicals such as organochlorine pesticides such as polychlorinated biphenyls (PCBs), polychlorinated dibenzo-p-dioxins (PCDDs), and polychlorinated dibenzofurans (PCDFs) or dioxin, which belong to persistent organic pollutants (POPs) in the endocrine disrupting chemicals.

Further, a research result that exposure to dioxin which is the most well-known among POPs may increase the occurrence risk of type II diabetes had been reported from the Vietnam veterans exposed to defoliant, but a degree of the relevance is not great and thus the research result had not received much attention. When a research result that there is a strong relevance between low-concentration POPs of the extent which is exposed to the general population of the united states and the type II diabetes was reported in 2006, the relevance between the POPs and the diabetes has newly received attention.

Particularly, as the concentration of the POPs which are usually detected in the general population is increased, prevalence of the type II diabetes is increased 10 times or greater and as a result, a strong dose-response relationship is shown. In terms of traditional toxicology, the PCBs types which did not receive much attention in related studies show to have a stronger relevance therewith than types of dioxin which are known as the largest toxicity and in studies for people without diabetes, a research result that the POPs shows a consistent relevance with insulin resistance and metabolic syndromes has been reported.

However, in the case of the endocrine disrupting chemicals, that is, the POPs, these damages penetrate into the body by ingestion and skin contact with air and most of POPs are absorbed through the digestive tract and the damages caused by skin contact may be sufficiently defended by washing. As a result, a method of excreting the ingested POPs and drugs for treating diseases caused by the POPs are required.

SUMMARY

An aspect to be achieved by the present disclosure is to provide a pharmaceutical composition for preventing and treating endocrine disrupting chemicals-induced diseases.

(1) According to an aspect of the present disclosure, there is a method for treating endocrine disrupting chemicals-induced diseases including administrating Fsp27 protein-specific siRNA or a pharmaceutically acceptable salt thereof to patients requiring the siRNA or the salt.

(2) The sequence of the Fsp27 protein is SEQ ID NO: 1 or 2.

(3) The Fsp27 protein-specific siRNA or the pharmaceutically acceptable salt thereof is administrated with an effective dose of 0.1 to 10 mg/Kg once.

(4) The Fsp27 protein-specific siRNA or the pharmaceutically acceptable salt thereof is administrated 7 to 21 times per week.

(5) The Fsp27 protein-specific siRNA or the pharmaceutically acceptable salt thereof is administrated parenterally.

(6) The method for treating endocrine disrupting chemicals-induced diseases further includes additionally administrating metformin or a pharmaceutically acceptable salt thereof.

(7) The metformin or the pharmaceutically acceptable salt thereof is administrated orally or parenterally.

(8) The metformin or the pharmaceutically acceptable salt thereof is administrated with an effective dose of 0.1 to 100 mg/Kg once.

(9) The metformin or the pharmaceutically acceptable salt thereof is administrated 7 to 21 times per week.

(10) The metformin or the pharmaceutically acceptable salt thereof is administrated together with the Fsp27 protein-specific siRNA or the pharmaceutically acceptable salt thereof.

(11) The endocrine disrupting chemicals-induced diseases are one or more diseases selected from a group consisting of obesity, insulin resistance, and type II diabetes.

(12) The endocrine disrupting chemical is polychlorinated biphenyl.

(13) According to another aspect of the present disclosure, there is a method for excreting endocrine disrupting chemicals including adding Fsp27 protein-specific siRNA to tissues including the endocrine disrupting chemicals.

(14) The method for excreting endocrine disrupting chemicals further includes adding metformin or a pharmaceutically acceptable salt thereof.

(15) The endocrine disrupting chemical is polychlorinated biphenyl.

(16) According to yet another aspect of the present disclosure, there is a pharmaceutical composition including Fsp27 protein-specific siRNA or a pharmaceutically acceptable salt thereof.

(17) The pharmaceutical composition further includes metformin or a pharmaceutically acceptable salt thereof.

(18) The Fsp27 protein-specific siRNA or the pharmaceutically acceptable salt thereof is included with 1 nM to 100 nM.

(19) The metformin or the pharmaceutically acceptable salt thereof is included with 2 mM to 15 mM.

(20) The sequence of the Fsp27 protein is SEQ ID NO: 1 or 2.

According to the present disclosure, since the composition has an effect of decreasing lipid accumulation caused by endocrine disrupting chemicals, for example, persistent organic pollutants (POPs) including polychlorinated biphenyl and the like and can improve insulin resistance caused by the POPs through reduction of insulin receptor substrate 1 (IR1), the composition can be helpfully used for treating diseases including obesity, insulin resistance, and the like induced by the endocrine disrupting chemicals. Further, according to the present disclosure, the composition has an effect of excreting the endocrine disrupting chemicals.

The effects of the present disclosure are not limited to the aforementioned effects, and various other effects are included in the present specification.

BRIEF DESCRIPTION OF THE DRAWINGS

The above and other aspects, features and other advantages of the present disclosure will be more clearly understood from the following detailed description taken in conjunction with the accompanying drawings, in which:

FIGS. 1A to 1G illustrate that PCB-118 and PCB-138 increase adipose mass and adipocyte size in C57BL/6 mice. FIGS. 1A to 1G shows the body weight (FIG. 1A), the liver weight (FIG. 1B), the body fat (FIG. 1C), and the percent body fat (FIG. 1D) of mice administered either vehicle (corn oil) or 37.5 mg/kg PCBs (PCB-118 or -138) for 6 weeks. FIG. 1E shows the exposed ventral view of representative mice from each group. FIG. 1F shows the representative H&E-stained sections of eWAT. Bar=100 μm. FIG. 1G shows the average adipocyte size of eWAT measured from H&E images using ImageJ 1.48q. n=5-10 per group. $*p<0.05$ and $**p<0.01$ compared with the experimental controls.

FIGS. 2A to 2G shows that PCB-118 and PCB-138 promote large LD formation. FIGS. 2A to 2G shows LD morphologies determined using inverted phase contrast microscopy (FIG. 2A), Oil-Red O staining (FIG. 2B), confocal microscopy (FIG. 2C) (upper, immunofluorescence staining with anti-perilipin antibody; lower, Nile Red staining) demonstrated that PCB-118 and PCB-138 increased LD size in 3T3-L1 adipocytes. In FIG. 2D, In FIG. 2E, the LD size distribution demonstrated that the population of LDs with a diameter 4-6 and >6 μm increased in PCB-treated 3T3-L1 adipocytes. Data were collected from 30 cells stained with BODIPY 493/503 in each group. Bar=10 μm. In FIGS. 2F and 2G, the western blot demonstrated that PCB-118 and PCB-138 increased the expression level of LD-associated proteins in PCBs-treated 3T3-L1 adipocytes (FIG. 2F) and mice (FIG. 2G).

FIGS. 3A to 3D shows that Fsp27 mediates PCB-induced LD enlargement. Inverted phase contrast microscopy (FIG. 3A) and confocal microscopy (FIG. 3B) demonstrated that siFsp27 markedly reversed PCB-induced LD enlargement. The data of LD size distribution were collected from 30 cells stained with BODIPY 493/503 in each group. (See FIG. 3C.) Bar=10 μm. ORO staining demonstrated that siFsp27 significantly decreased total lipid content in PCB-treated 3T3L1 adipocytes. $**p<0.01$ compared with the experimental controls (FIG. 3D).

FIGS. 4A to 4E show that PCB-118 and PCB-138 impair insulin action. Blood glucose level (FIG. 4A) and plasma insulin level (FIG. 4) were significantly higher in PCB-administered mice. n=7-10 per group. The blood glucose levels over the entire time course of the GTT (FIG. 4C) and ITT (FIG. 4D) were significantly higher in PCB-administered (PCB-118 or PCB-138) mice. n=7-10 per group. $*p<0.05$ and $**p<0.01$ compared with the experimental controls. In FIG. 4E, the western blot demonstrated that PCB-118 and PCB-138 impaired the insulin-induced upregulation of p-Akt(S473) and p-PI3K p85(Y458) in 3T3-L1 adipocytes.

In FIGS. 5A and 5B, the western blot (upper) demonstrated that the protein level but not mRNA level (lower) of IRS1 was reduced in PCB-administered mice (FIG. 5A) and PCB-treated 3T3-L1 adipocytes (FIG. 5B). In FIG. 5C, Western blot demonstrated that siFsp27 reversed PCB-induced IRS1 downregulation. n=4. In FIG. 4D, Western blot bands were quantified and normalized to anti-actin control bands using ImageJ 1.48q. $**p<0.01$ compared with the experimental controls (FIG. 5D).

FIGS. 6A to 6E show that metformin reduces LD size and increases IRS1 protein level in PCB-treated 3T3-L1 adipocytes through downregulation of Fsp27 expression. In FIG. 6A, the western blot demonstrated that metformin not only reduced Fsp27 protein level, but reversed PCB-induced upregulation of Fsp27 protein. In FIG. 6B, the phase contrast microscopy demonstrated that metformin markedly reduced PCB-induced LD enlargement. Bar=10 μm. In FIG. 6C, the western blot demonstrated that the reversal by metformin of Fsp27 upregulation was correlated with the reversal by metformin of IRS1 downregulation. n=3. In FIG. 6D, the western blot bands were quantified and normalized to anti-actin control bands using ImageJ 1.48q. $*p<0.05$ and $**p<0.01$ compared with the experimental controls. In FIG. 6E, the western blot demonstrated that metformin reversed the impairment by PCBs of the insulin-induced upregulation of p-Akt (Ser473) and p-PI3K 488 p85(Tyr458).

DETAILED DESCRIPTION

Figure 1B:
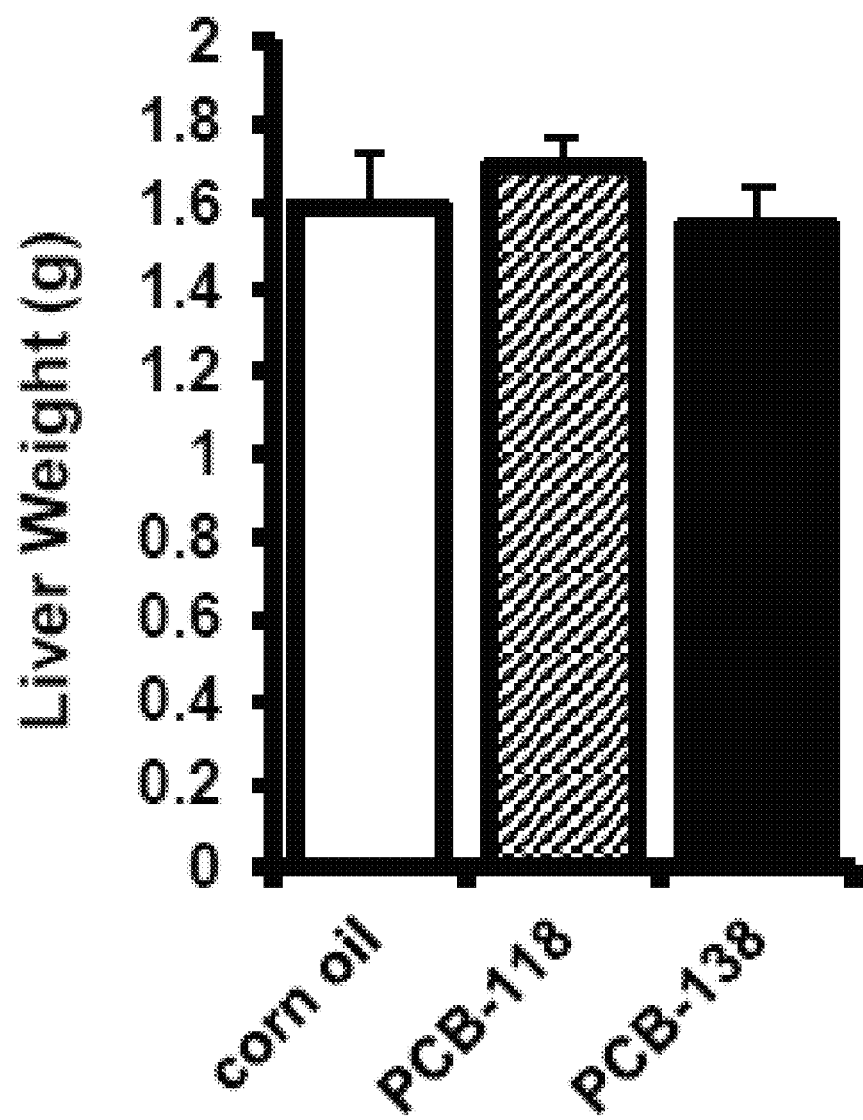

Hereinafter, various aspects and various exemplary embodiments of the present disclosure will be described in more detail.

The present disclosure provides a method for treating endocrine disrupting chemicals-induced diseases including administrating Fsp27 protein-specific siRNA or a pharmaceutically acceptable salt thereof to patients requiring the siRNA or the salt.

According to an exemplary embodiment of the present disclosure, when the patient is exposed to polychlorinated biphenyl among the endocrine disrupting chemicals, it is verified that adipocytes are increased, lipid droplets are enlarged, and there is insulin resistance, and it is reported that the endocrine disrupting chemicals cause an increase in body weight through a variety of mechanisms including a set point change of metabolic homeostasis, stimulating an appetite center, and decreasing mitochondria function, and the like.

Further, the obesity induced by the endocrine disrupting chemicals causes insulin resistance and increases compensatively insulin secretion from beta cells of the pancreas in the initial stage to maintain normal blood glucose, but the insulin resistance state is maintained, and as a result, failure in the insulin secretion of the beta cells of the pancreas occurs and type II diabetes is caused together with increased blood sugar. Further, the insulin resistance is considered as a key factor causing metabolic syndromes such as type II diabetes, hypertension, dyslipidemia, low HDL cholesterolemia, and cardiovascular disease.

Meanwhile, the insulin resistance is that a function of insulin lowering blood sugar is deteriorated and therefore, cells do not efficiently burn glucose. When the insulin resistance is high, the human body creates too much insulin and as a result, may cause heart disease, diabetes, and the like in addition to hypertension or dyslipidemia. Particularly, in the type II diabetes, there is a problem in that an increase in insulin is not detected in muscles and adipose tissues and thus action of the insulin does not occur.

When administrating Fsp27 protein-specific siRNA or a pharmaceutically acceptable salt thereof to patients requiring the siRNA or the salt which is proposed as a method for treating endocrine disrupting chemicals-induced diseases including obesity, insulin resistance, and the like is performed, the composition has an effect of decreasing lipid accumulation caused by the endocrine disrupting chemicals and can improve insulin resistance through reduction of insulin receptor substrate 1 (IR1), and as a result, the composition can be helpfully used for treating diseases including obesity, insulin resistance, and the like induced by the endocrine disrupting chemicals.

The sequence of the Fsp27 protein according to the present disclosure may be SEQ ID NO: 1 or 2.

In the present disclosure, the Fsp27 protein-specific siRNA or the pharmaceutically acceptable salt thereof may be administrated parenterally, for example, by a subcutaneous injection.

The Fsp27 protein-specific siRNA or the pharmaceutically acceptable salt thereof may be administrated with an appropriate dose, for example, an effective dose of 0.1 to 10 mg/Kg once and administrated 7 to 21 times per week.

The method for treating endocrine disrupting chemicals-induced diseases according to the present disclosure may further include additionally administrating metformin or a pharmaceutically acceptable salt thereof.

In the present disclosure, the metformin or the pharmaceutically acceptable salt thereof may be orally administrated.

The metformin may be administrated with an effective dose of 0.1 to 100 mg/Kg once a day and preferably administrated 7 to 21 times per week. For oral administration, the metformin may be formulated to solid administration forms such as tablets or pills.

In the present disclosure, the metformin or the pharmaceutically acceptable salt thereof may be administrated together with the Fsp27 protein-specific siRNA or the pharmaceutically acceptable salt thereof.

The patients to be treated by the method of the present disclosure may be adult patients. The age of the corresponding patients may be 18 to 50.

The endocrine disrupting chemicals-induced diseases according to the present disclosure may be one or more diseases selected from a group consisting of obesity, insulin resistance, and type II diabetes, and the endocrine disrupting chemical may be polychlorinated biphenyl.

In the present disclosure, the pharmaceutically acceptable salt may include an acid addition salt formed by pharmaceutically acceptable free acid, and as the free acid, both inorganic acid and organic acid may be used. The used inorganic acid includes hydrochloric acid, bromic acid, sulfuric acid, phosphoric acid, and the like, and the used organic acid includes citric acid, acetic acid, lactic acid, maleic acid, umarine acid, gluconic acid, methanesulfonic acid, glycolate, succinate, 4-toluenesulfonic acid, trifluoroacetic acid, galacturonic acid, embonate, glutamic acid, aspartic acid, and the like.

Further, the present disclosure provides a method for excreting endocrine disrupting chemicals including adding Fsp27 protein-specific siRNA to tissues including the endocrine disrupting chemicals.

In the present disclosure, the Fsp27 protein-specific siRNA further includes metformin or a pharmaceutically acceptable salt thereof and may be added to the tissues including the endocrine disrupting chemicals to excrete the endocrine disrupting chemicals.

The endocrine disrupting chemical may be polychlorinated biphenyl.

The endocrine disrupting chemicals may have an effect on reproduction by preventing normal hormones from being created or acting on in our bodies and thus should be rapidly excreted, however, there is a problem in that persistent organic compounds such as polychlorinated biphenyl are not easily decomposed.

Figure 7A:
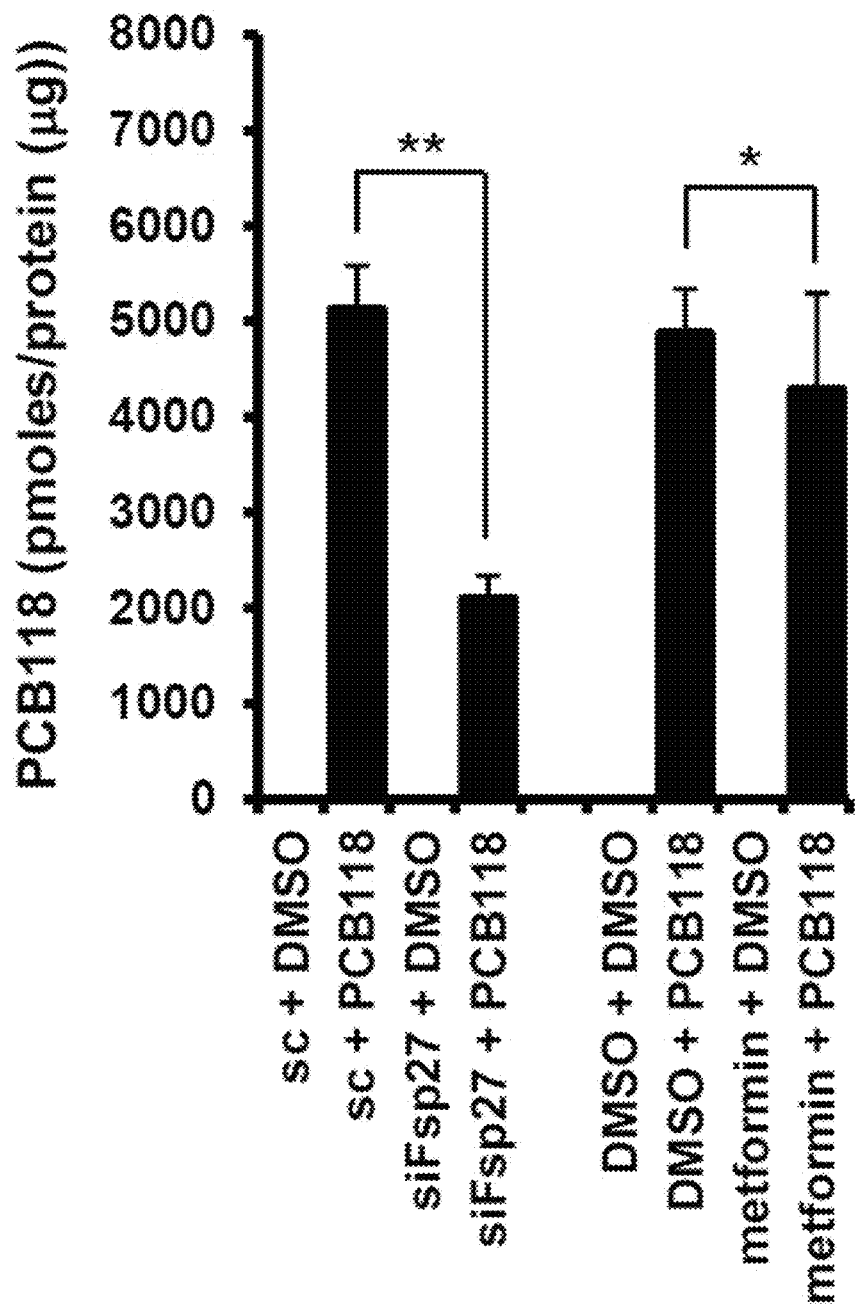
FIGS. 7A and 7B illustrate that the composition of the present disclosure has an effect of excreting endocrine disrupting chemicals in vivo, preferably polychlorinated biphenyl accumulated in adipocytes.
Figure 7B:
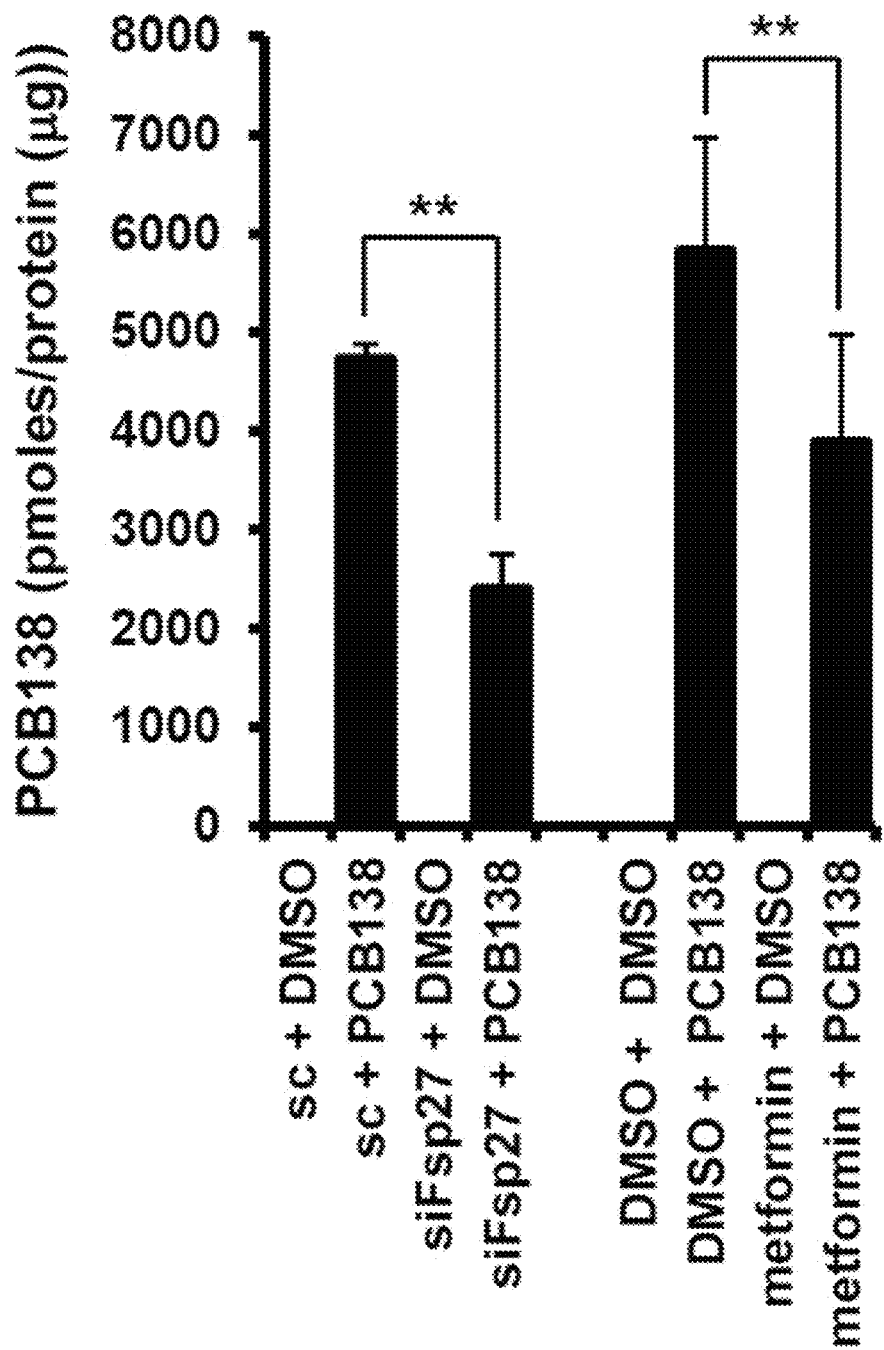

As described above, it can be seen that the composition of the present disclosure has an effect of excreting endocrine disrupting chemicals in vivo, preferably polychlorinated biphenyl accumulated in adipocytes, as illustrated in FIGS. 7A and 7B.

Further, the present disclosure provides a pharmaceutical composition including Fsp27 protein-specific siRNA or a pharmaceutically acceptable salt thereof.

As described above, the composition according to the present disclosure has an effect of decreasing lipid accumulation caused by the endocrine disrupting chemicals and can improve insulin resistance through reduction of insulin receptor substrate 1 (IR1), and thus the composition can be helpfully used for treating diseases including obesity, insulin resistance, and the like induced by the endocrine disrupting chemicals.

In the present disclosure, the pharmaceutical composition may further include metformin or a pharmaceutically acceptable salt thereof.

The Fsp27 protein-specific siRNA or the pharmaceutically acceptable salt thereof may be included with an intercellular concentration of 1 nM to 100 nM.

In the case of deviating from the range, when the concentration of the Fsp27 protein-specific siRNA or the pharmaceutically acceptable salt thereof deviates from the range, or when the concentration thereof is less than 1 nM, it is difficult to decrease lipid accumulation caused by the endocrine disrupting chemicals or it may be difficult to excrete the endocrine disrupting chemicals. When the concentration thereof is greater than 100 nM, there is a problem in that the Fsp27 protein-specific siRNA or the pharmaceutically acceptable salt thereof may rather have cytotoxicity.

Further, when the metformin or the pharmaceutically acceptable salt thereof is additionally included, the metformin or the pharmaceutically acceptable salt thereof may be included with 2 mM to 15 mM.

In the case of deviating from the range, when the metformin or the pharmaceutically acceptable salt thereof deviates from the range, it is difficult to improve insulin resistance caused by the targeted endocrine disrupting chemicals.

The sequence of the Fsp27 protein according to the present disclosure may be SEQ ID NO: 1 or 2.

In the present disclosure, as described above, the pharmaceutical composition may be used for treating diseases such as obesity or insulin resistance induced by the endocrine disrupting chemicals.

The endocrine disrupting chemicals may be persistent organic pollutants, and preferably, the persistent organic pollutants may be polychlorinated biphenyls, for example, PCB-153, PCB-138, PCB-180, PCB-170, PCB-118, PCB-156, and the like.

In the present disclosure, the endocrine disrupting chemicals-induced diseases may be one or more selected from a group consisting of obesity, insulin resistance, and type II diabetes.

Hereinafter, the present disclosure will be described in more detail through Examples, but it can not be interpreted that the scope and the contents of the present disclosure are reduced or restricted by Examples below. Further, based on the disclosed contents of the present disclosure including Examples below, particularly, it is apparent that the present disclosure in which experimental results are not presented can be easily implemented by those skilled in the art and it is natural that these modifications and corrections belong to the appended claims.

Materials 3,3',4,4'-tetrachlorobiphenyl (PCB-77), 2,3',4,4',5-pentachlorobiphenyl (PCB-118), 2,2',3,4,4',5'-Hexachlorobiphenyl (PCB-138) and 2,2',4,4,5,5'-hexachlorobiphenyl (PCB-153) were purchased from AccuStandard Inc. (New Haven, Conn., USA). Mouse insulin ELISA kit was purchased from Shibayagi (Gunma, Japan). BODIPY 493/503 and Nile Red were purchased from Molecular Probes (Eugene, Oreg., USA). 3-isobutyl-1-methylxanthine (IBMX), dexamethasone (DEXA), insulin, metformin, Oil red O, corn oil and anti-beta-actin antibody were purchased from Sigma (St. Louis, Mo., USA). The Lipofectamine 2000 and Lipofectamine® RNAiMAX transfection reagents were purchased from Invitrogen (Carlsbad, Calif., USA). Anti-IRS1 (sc-559), C/EBP and GAPDH antibodies were purchased from Santa Cruz Biotechnology (Santa Cruz, Calif., USA). Anti-aP2, perilipin, PPAR, Akt1/2, phospho-Akt (Ser473), PI3K-p85, phospho-PI3K-p85 (Tyr458) antibodies were obtained from Cell Signaling (Danvers, Mass., USA). Anti-phospho-IRS1 (Ser307) antibodies were obtained from Upstate Biotechnology (Lake Placid, N.Y., USA). Anti-Fsp27 antibodies were obtained from Abcam (Cambridge, Mass., USA).

Animals and PCBs Exposure

Adult male C57BL/6 mice (8-week-old, 22-25 g) were purchased from SamTako Bio-Korea (Osan, Korea). The animals were maintained in a temperature-controlled room (22° C.) on a 12:12-h light-dark cycle. All procedures were approved by the Committee on Animal Investigations at Dong-A University. 12-week-old mice were administered vehicle (corn oil), PCB-118 or PCB-138 (37.5 mg/kg) by intraperitoneal (ip) injection for a total of three injections (2, 3 and 5 weeks) during the 6-week study duration. Mice were randomly divided into 3 groups of 10 animals each.

Cell Culture and Treatment

3T3-L1 mouse embryo fibroblasts, purchased from American Type Culture Collection (Manassas, Va., USA), were maintained in standard Dulbecco's modified Eagle's medium (DMEM; Gibco-BRL, Gaithersburg, Md., USA) supplemented with 10% fetal calf serum (FCS; Gibco-BRL, Gaithersburg, Md., USA) and 1% penicillin/streptomycin at 37° C. in a humidified 5% $CO_2$ atmosphere. After confluence, 3T3-L1 cells were induced to differentiate using DMI induction medium (DMEM containing 10% FBS, 0.5 mM 3-isobutyl-1-methylxanthine, 0.5 µM dexamethasone, and 1 µg/ml insulin) for 2 days, followed by DMII (DMEM containing 10% FBS and 1 µg/ml insulin) for 2 days. The medium was subsequently replaced with fresh culture medium (DMEM with 10% FBS) every 2 days for 4 days. To define the effects of PCBs on adipocyte differentiation, we incubated preadipocytes with PCBs (PCB-77, PCB-118, PCB-138 or PCB-153) at equivalent concentrations (20 µM) during DMI treatment.

RNA Interference and Transfection

For the siRNA-mediated down-regulation of Fsp27, Fsp27-specific siRNA and negative control siRNA were purchased from Bioneer (Daejeon, Korea) and used at a concentration of 20 nM. 3T3-L1 mouse embryo fibroblasts were transfected with either the siRNA molecule specific for Fsp27 or a negative control siRNA using Lipofectamine® RNAiMAX per the manufacturer's instructions.

Histology Staining

Epididymal white adipose tissues (eWAT) were fixed in 10% neutral buffered formalin and embedded in paraffin. Four-micrometer sections were prepared and stained with hematoxylin and eosin. The morphology of the liver tissue was photographed using an Aperio ScanScope (Aperio Technologies, Vista, Calif., USA).

Oil Red O Staining

As previously described (Kim et al. 2015), cells were washed twice in phosphate buffered saline (PBS) and fixed for 1 h with 10% (w/v) formaldehyde in PBS. After two washes in 60% isopropyl alcohol, the cells were stained for 30 min in freshly diluted Oil Red O solution. Then, the stain was removed, and the cells were washed 4 times in water. After adding 100% 2-propanol at 500 nm, the absorbance of the eluted Oil Red O was measured in a spectrophotometer.

Plasma Glucose Concentrations and Tolerance Tests for Glucose and Insulin

As previously described, intraperitoneal glucose tolerance tests (GTT) and insulin tolerance tests (ITT) were performed after the mice were fasted for 16 h. Plasma glucose concentrations were measured in tail blood using a GlucoDr Blood Glucose Test Strip (Hasuco, Seoul, South Korea) prior to and 30, 60, 90 and 120 minutes after intraperitoneally injecting a bolus of glucose (1 mg/g) for the GTT, and at the same time-points after intraperitoneally injecting 0.75 U/kg body weight insulin for the ITT.

RNA Isolation and RT-PCR

Total RNA was prepared from cell lines or tissues using TRIzol reagent (Invitrogen, Carlsbad, Calif., USA), according to the manufacturer's instructions. Then, 5 µg of total RNA was converted into single-stranded cDNA using MMLV reverse transcriptase (Promega, Madison, Wis., USA) with random hexamer primers. A one-tenth aliquot of cDNA was subjected to PCR amplification using gene-specific primers.

Western Blot Analysis

Cells and tissues were washed with ice-cold PBS, resuspended in 100 µL ice-cold RIPA buffer and incubated at 4° C. for 30 min. Lysates were centrifuged at 13,000 rpm for 30 min at 4° C. Equal amounts of proteins were subjected to 7.5-15% sodium dodecyl sulfate polyacrylamide gel electrophoresis. The proteins were transferred to a nitrocellulose membrane and reacted with each antibody. Immunostaining with antibodies was performed using the Super Signal West Pico (Thermo Scientific, Hudson, N.H., USA) enhanced chemiluminescence substrate and detected with LAS-3000 Plus (Fuji Photo Film, Tokyo, Japan). Quantification and normalization to actin or GAPDH control bands were performed using ImageJ 1.48q (NIH imaging software, Bethesda, Md., USA).

Statistical Analysis

At least three independent experiments were conducted. The results are expressed as the means±standard deviations (±SD). The statistical significance of the differences was determined using a Mann-Whitney U test. P<0.05 indicated statistical significance.

Results

PCBs Promote Adipocyte Differentiation in 3T3-L1 Adipocytes

Using four types of PCBs (PCB-77, PCB-118, PCB-138 and PCB-153), we examined the effects of PCBs at equivalent concentrations (20 μM) on the differentiation of 3T3-L1 adipocytes. Among these four types, PCB-118 and PCB-138 significantly increased oil red 0 staining. Thus, PCB-118 and PCB-138 were utilized in further in vitro and in vivo studies. In vitro, PCB-118 and PCB-138 increased both mRNA and protein levels of aP2, PPAR☐and C/EBP☐which are markers of adipocyte differentiation. These results indicate that PCB-118 and PCB-138 promote adipogenesis in vitro.

PCB-118 and PCB-138 Increase Adipose Mass and Adipocyte Size in C57BL/6 Mice

Figure 1C:
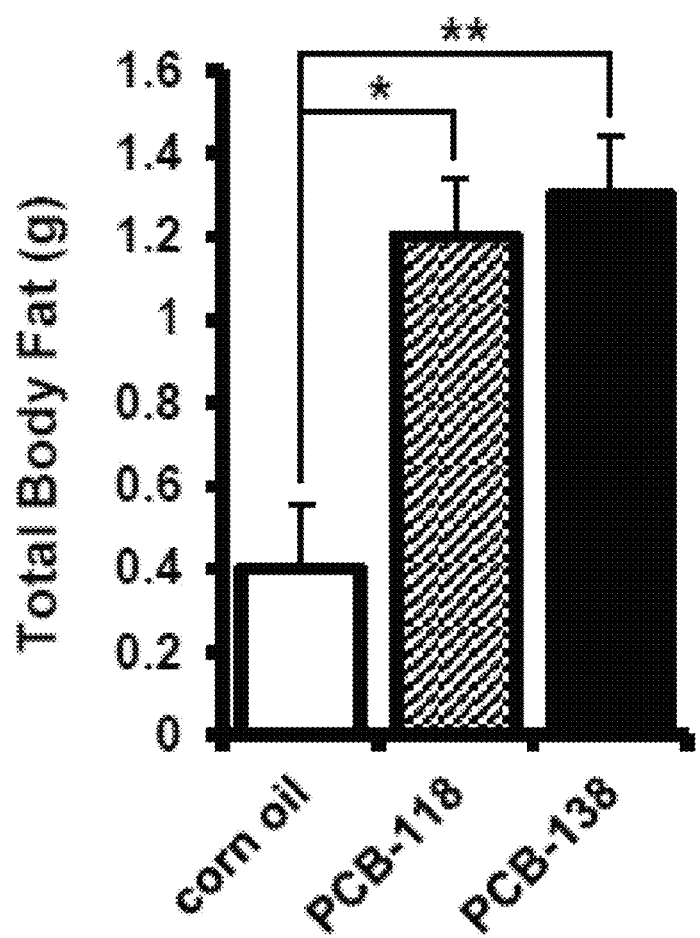
Figure 1D:
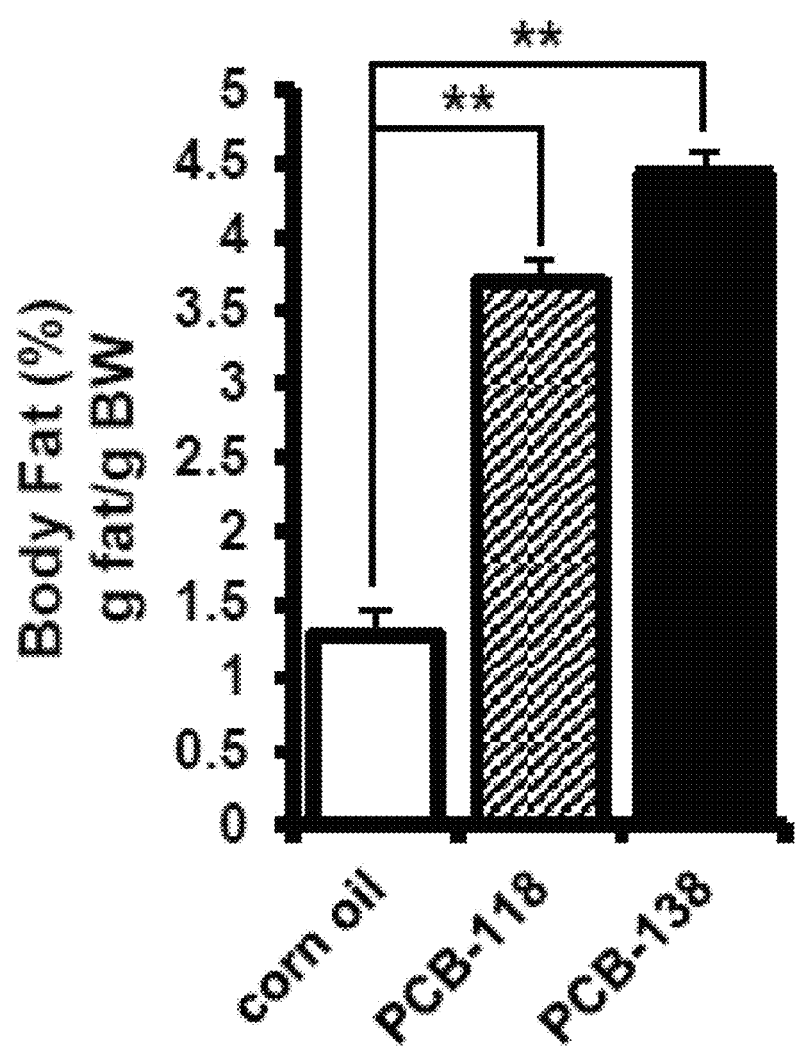
Figure 1E:
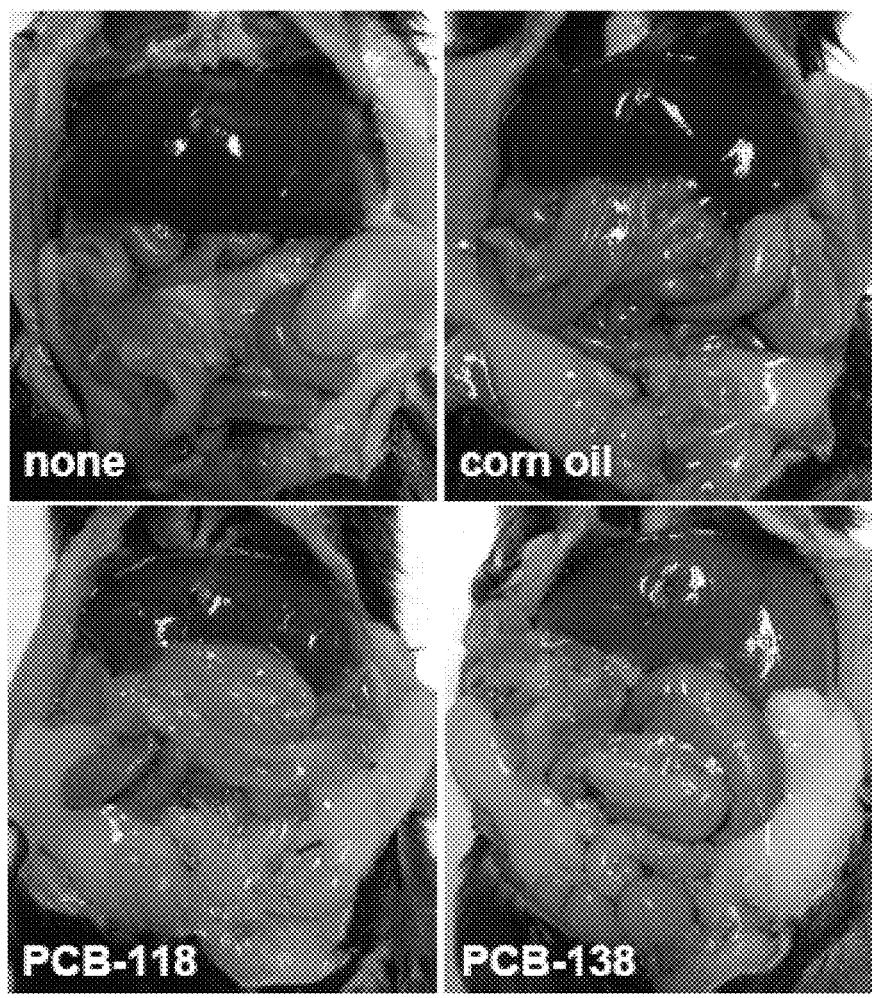
Figure 1F:
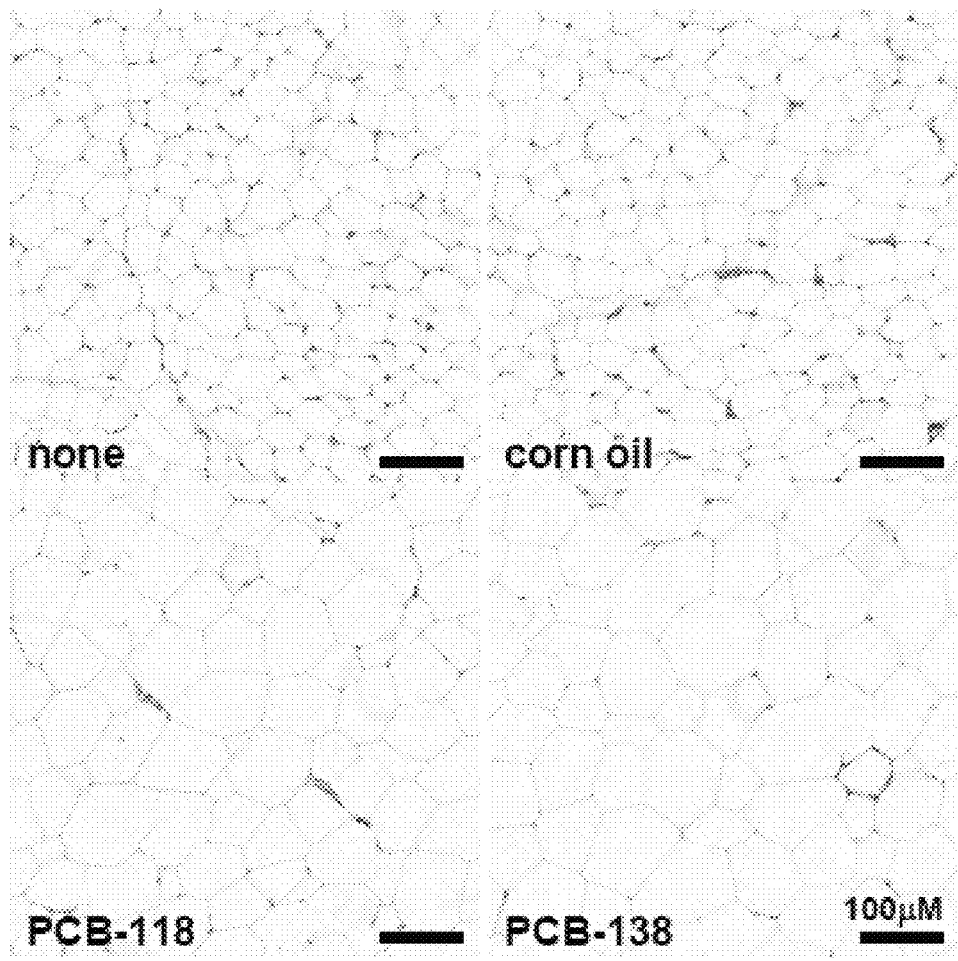
Figure 1G:
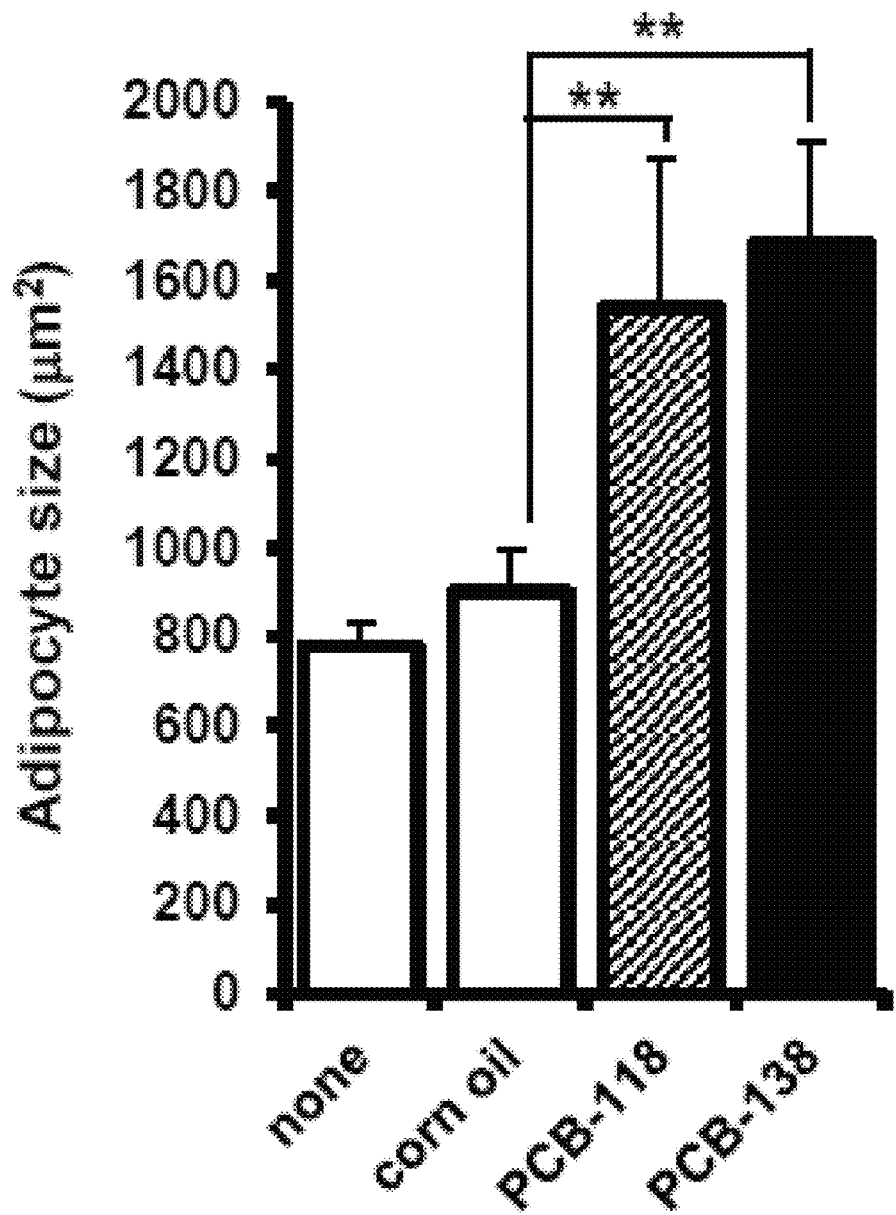

To determine whether PCB (PCB-118 or PCB-138) exposure affects adiposity, adult male C57BL/6 mice were administered PCB-118 or PCB-138 (37.5 mg/kg) by intraperitoneal injection. Both PCB-118 and PCB-138 increased adipose mass (FIGS. 1C to 1E) and adipocyte size (FIGS. 1F and 1G) without affecting body weight (FIG. 1A) or liver weight (FIG. 1B).

PCBs Promote Large LD Formation

Figure 2E:
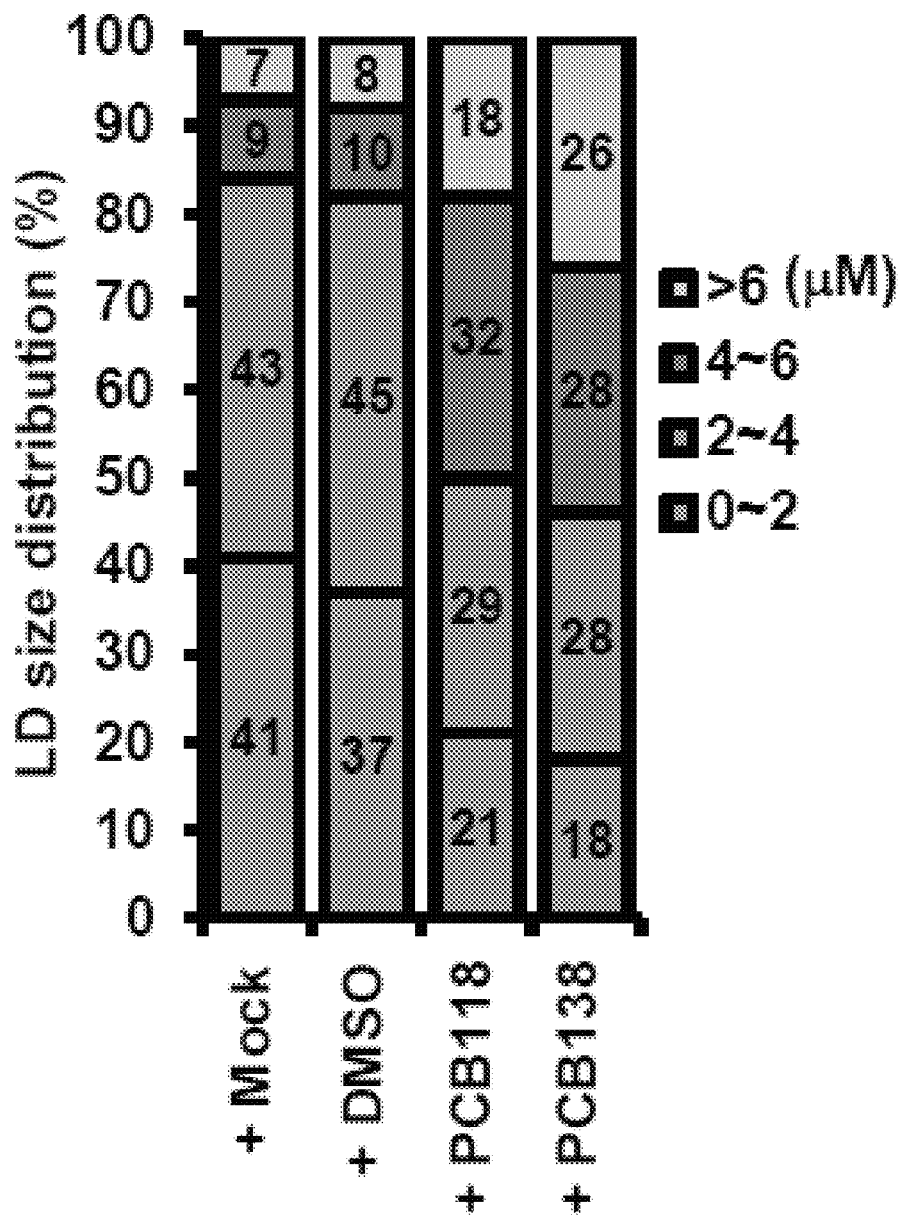
Figure 2F:
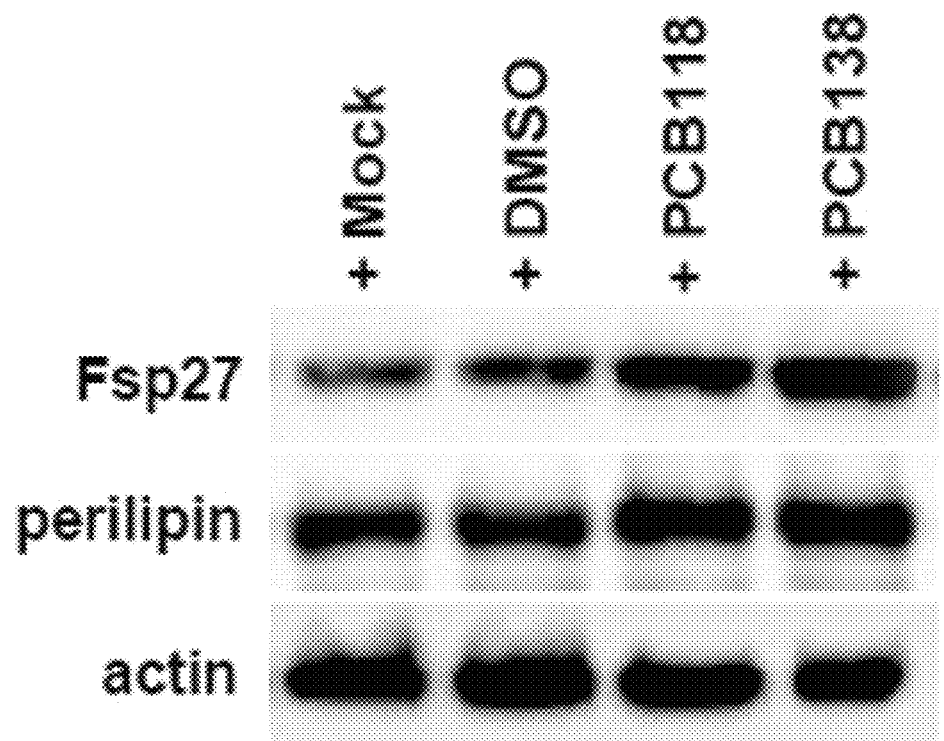
Figure 2G:
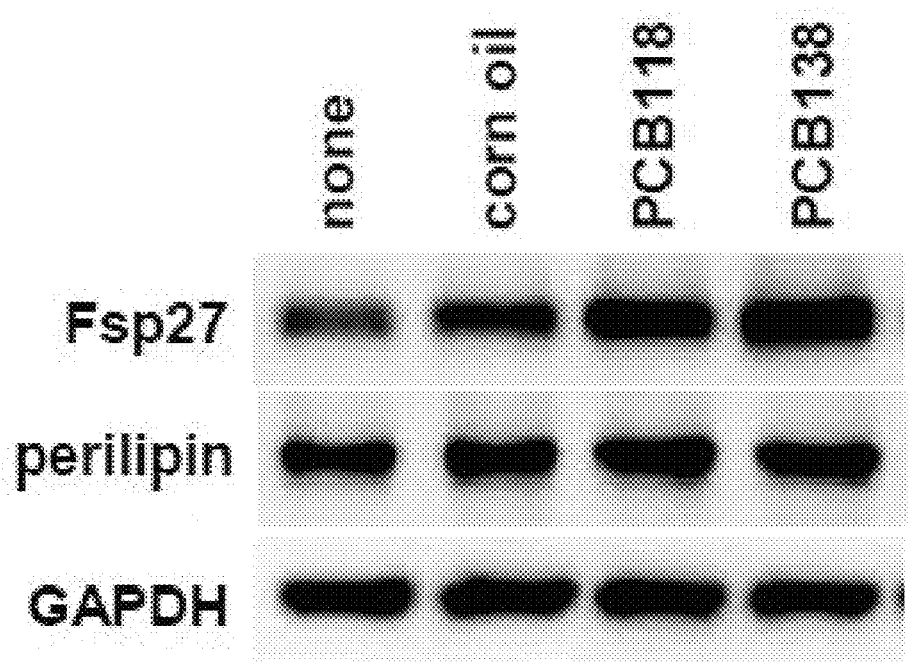

Phase contrast microscopy, oil red O stain, and confocal microscopy demonstrated that numerous small LDs appear in control adipocytes. Importantly, fewer and larger LDs were formed in adipocytes treated with PCBs (FIGS. 2A to 2C). Our analysis on the size distribution of the LDs corroborate that PCBs promote large LD formation (FIG. 2D). Western blot assay showed that PCB-118 and PCB-138 increased protein expression levels of Fsp27 and perilipin, which are the proteins associated with the surface of the intracellular LD in vitro (FIG. 2F) and in vivo (FIG. 2G). These results indicate that PCB-118 and PCB-138 promote large LD formation.

Fsp27 Mediates PCB-Induced LD Enlargement

Figure 3B:
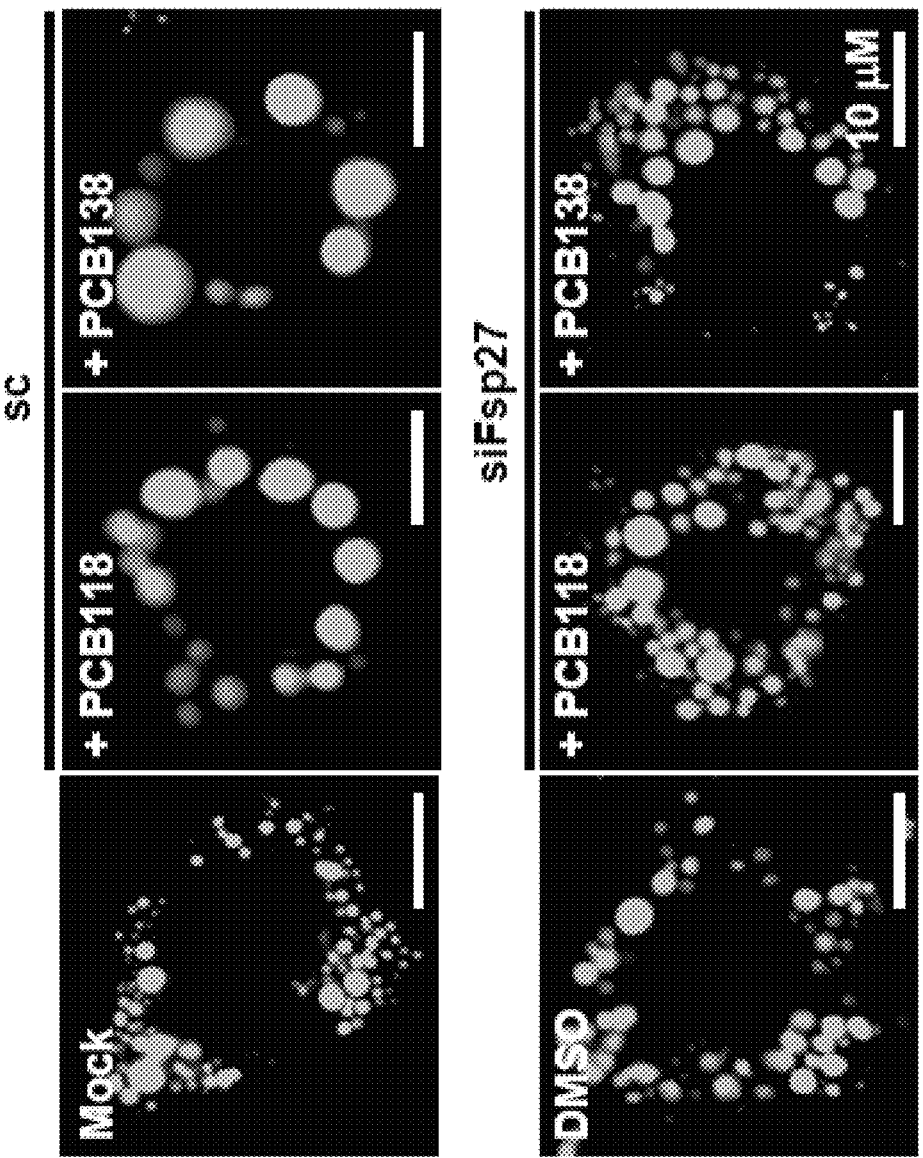
Figure 3C:
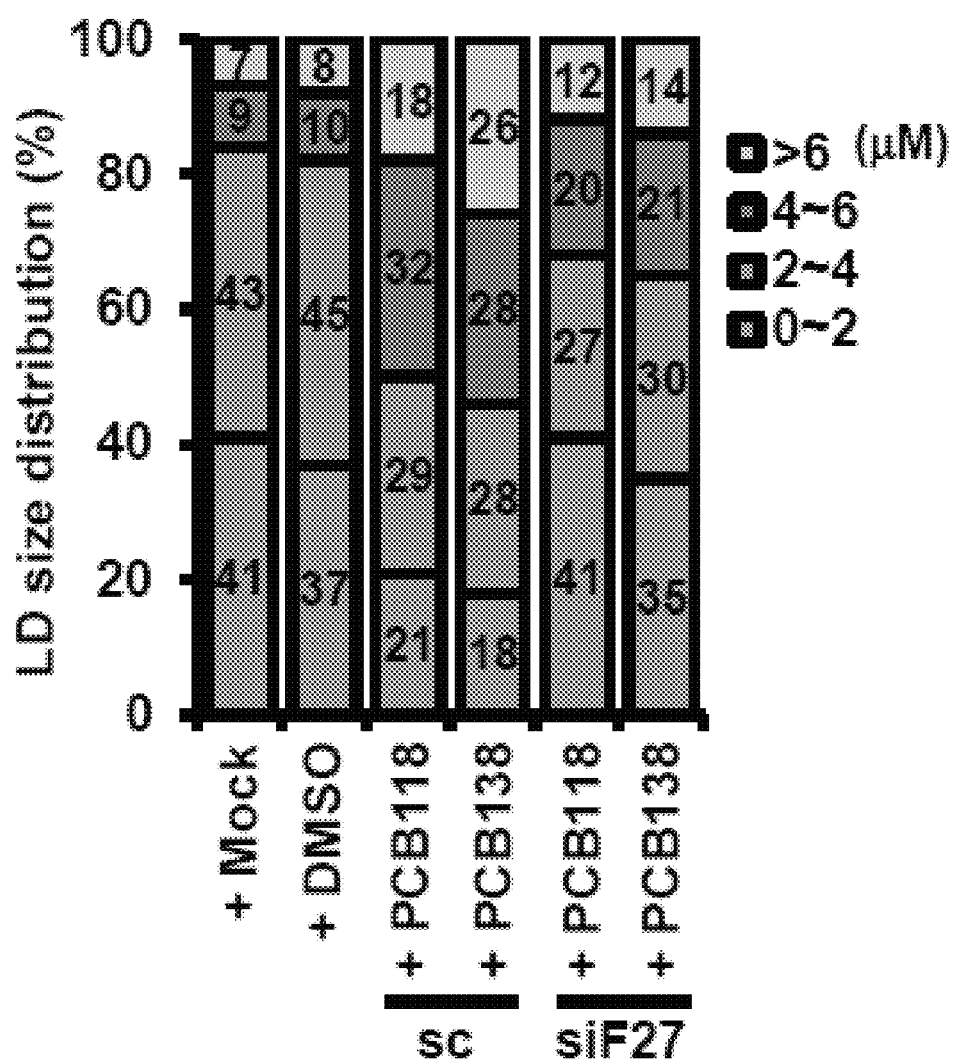
Figure 3D:
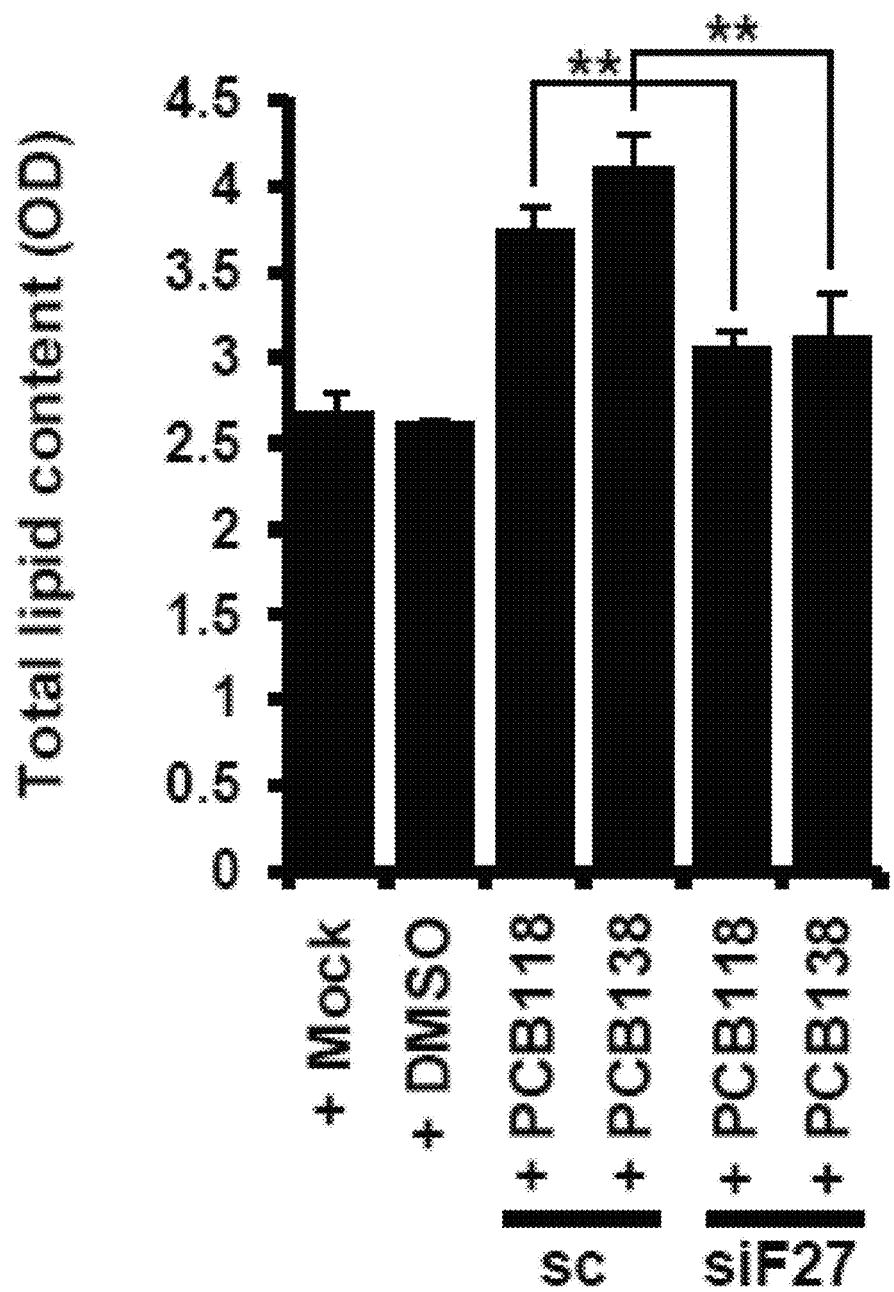

We next examined whether PCB-induced large LD formation is mediated by Fsp27. Noticeably, more numerous and smaller LDs were observed in Fsp27-depleted adipocytes compared to experimental controls (FIGS. 3A and 3B). Total lipid content is decreased by siFsp27 in PCB-treated 3T3L1 adipocytes (FIG. 3C). These data suggest that siFsp27 prevented the enlargement of lipid droplets in adipocytes treated with PCB-118 and PCB-138, indicating that Fsp27 mediates PCB-induced LD enlargement.

PCBs Impair Insulin Action

Figure 4C:
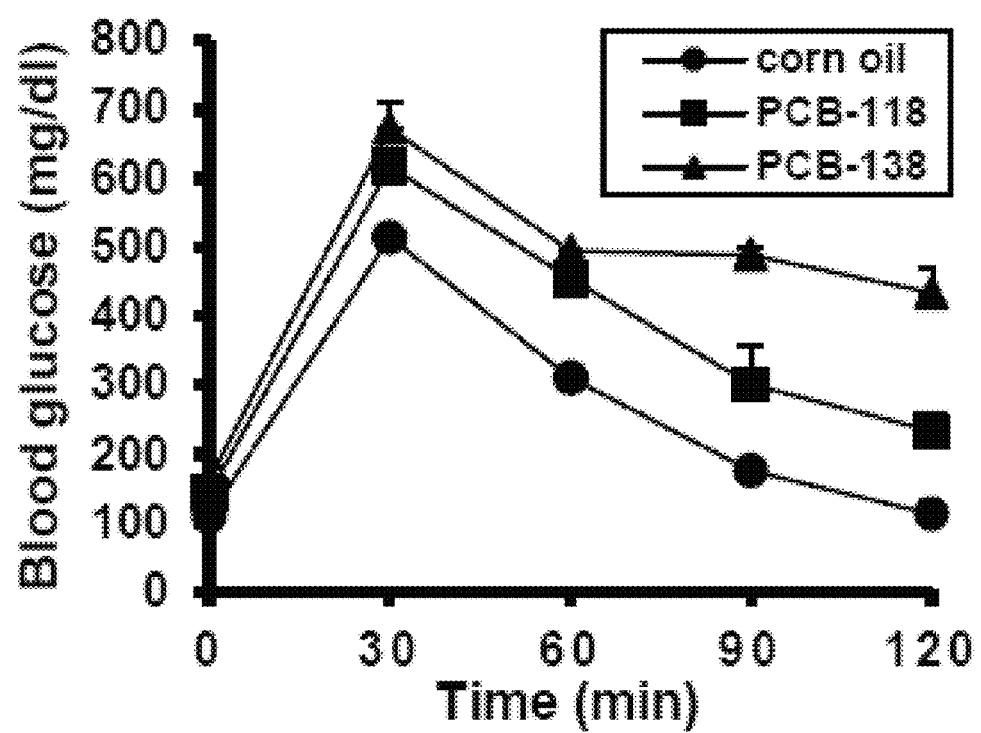
Figure 4D:
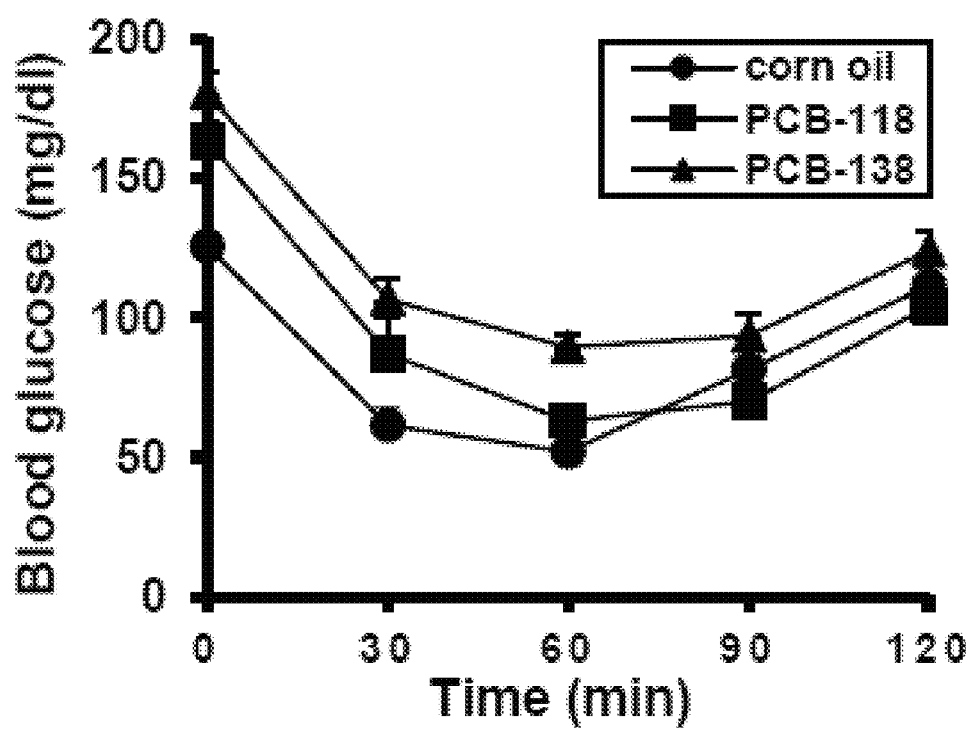
Figure 4E:
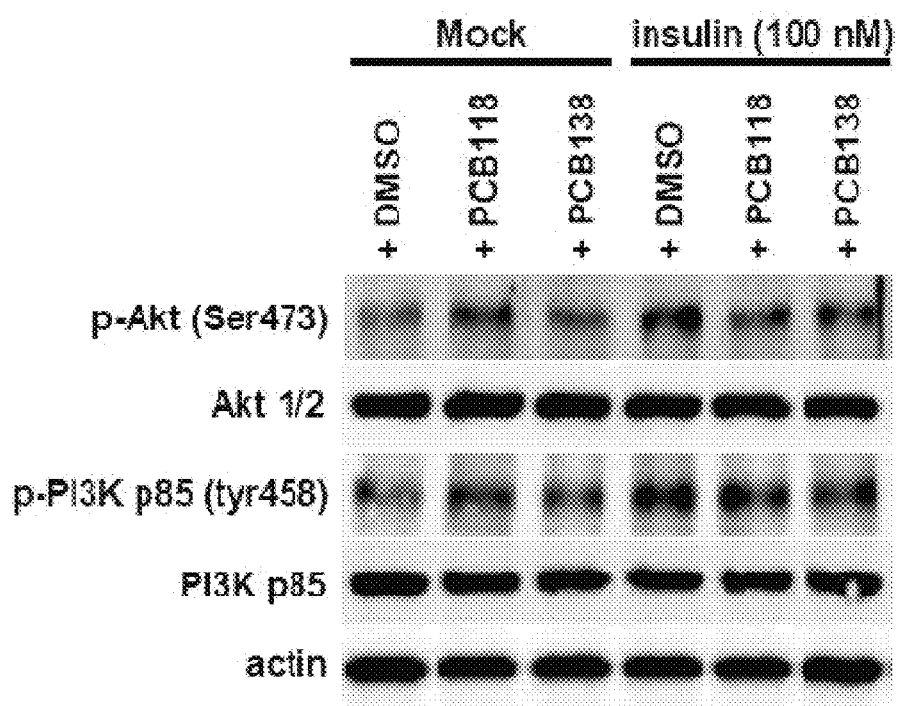

Next, we assessed the impacts of PCBs (PCB-118 or PCB-138) on insulin action in vivo and in vitro. Both PCBs increased blood glucose level (FIG. 4A) and plasma insulin level (FIG. 4B). Furthermore, the amount of hyperglycemia in GTT (FIG. 4C) was increased and the efficiency of insulin in ITT (FIG. 4D) was reduced in PCB-administered mice. We further determined the signaling pathway by which PCBs induce the development of insulin resistance. Both PCBs impaired the insulin-induced upregulation of p-Akt (Ser473) and p-PI3K p85 (Tyr458) in 3T3-L1 adipocytes (FIG. 4E). We further examined whether PCB-77 and PCB-153, which showed the meager effect on the adipocyte differentiation compared to PCB-118 and PCB-138, also affects the insulin action in adipocytes.

Fsp27 Mediates PCB-Induced Insulin Resistance Via IRS1 Downregulation

Figure 5A:
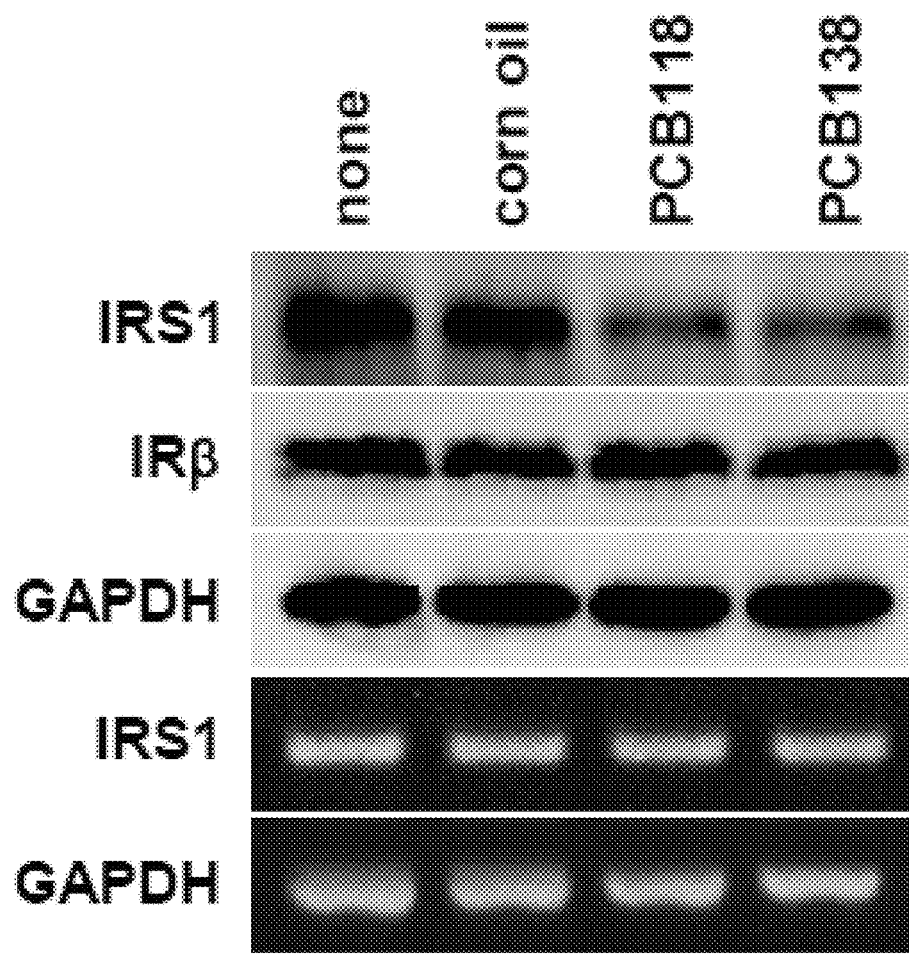
FIGS. 5A to 5D show that Fsp27 mediates PCB-induced (PCB-118 or -138) IRS1 downregulation.
Figure 5B:
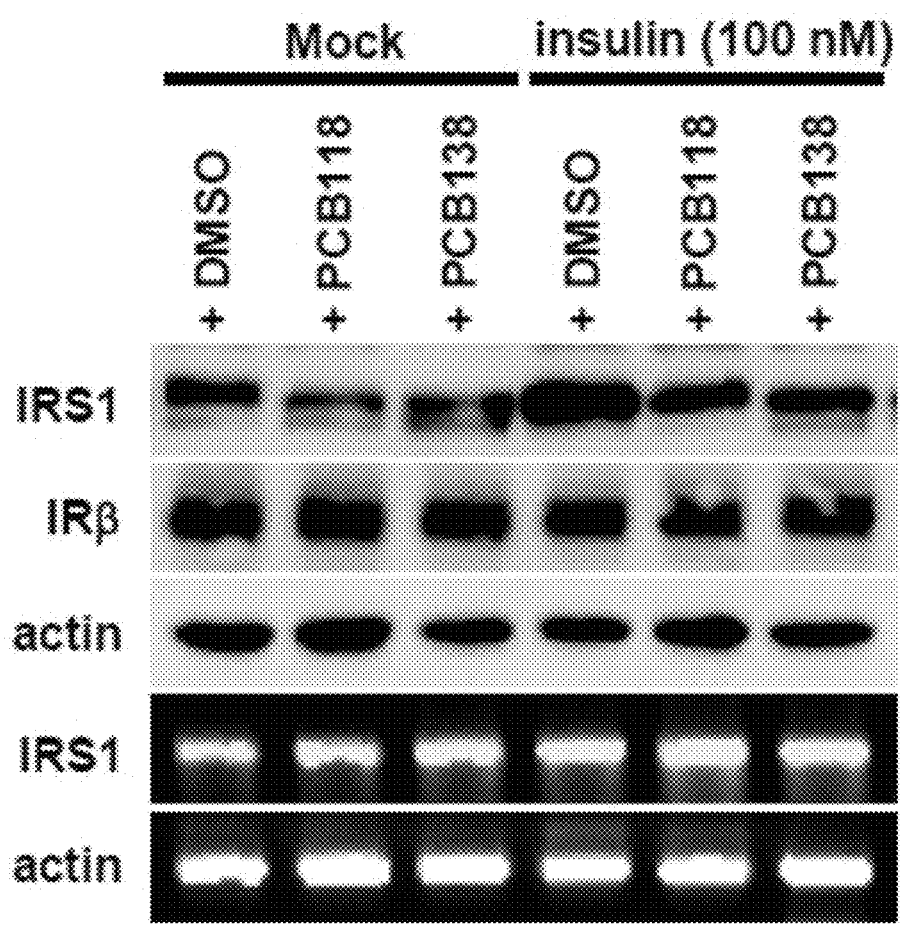
Figure 5C:
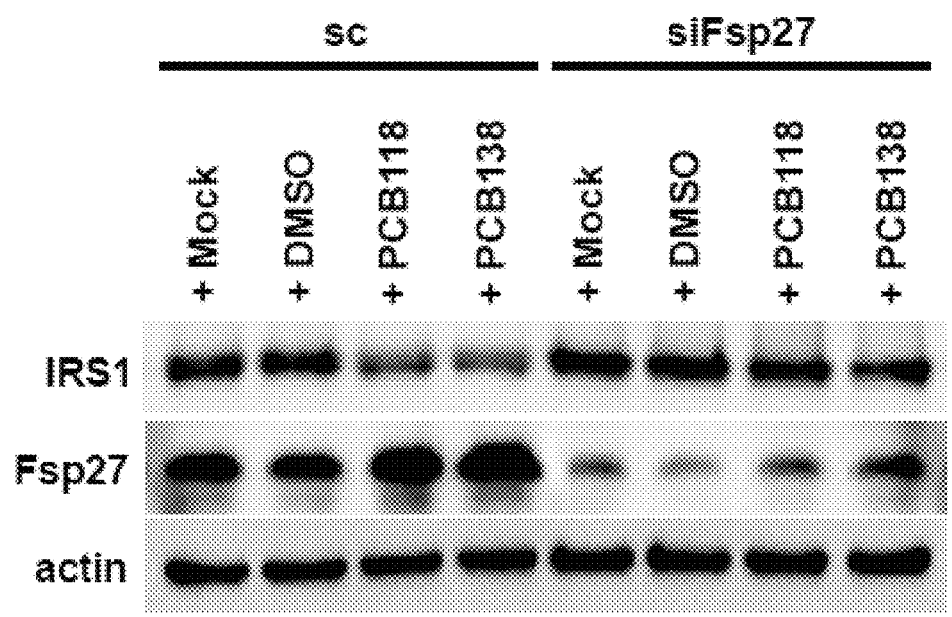
Figure 5D:
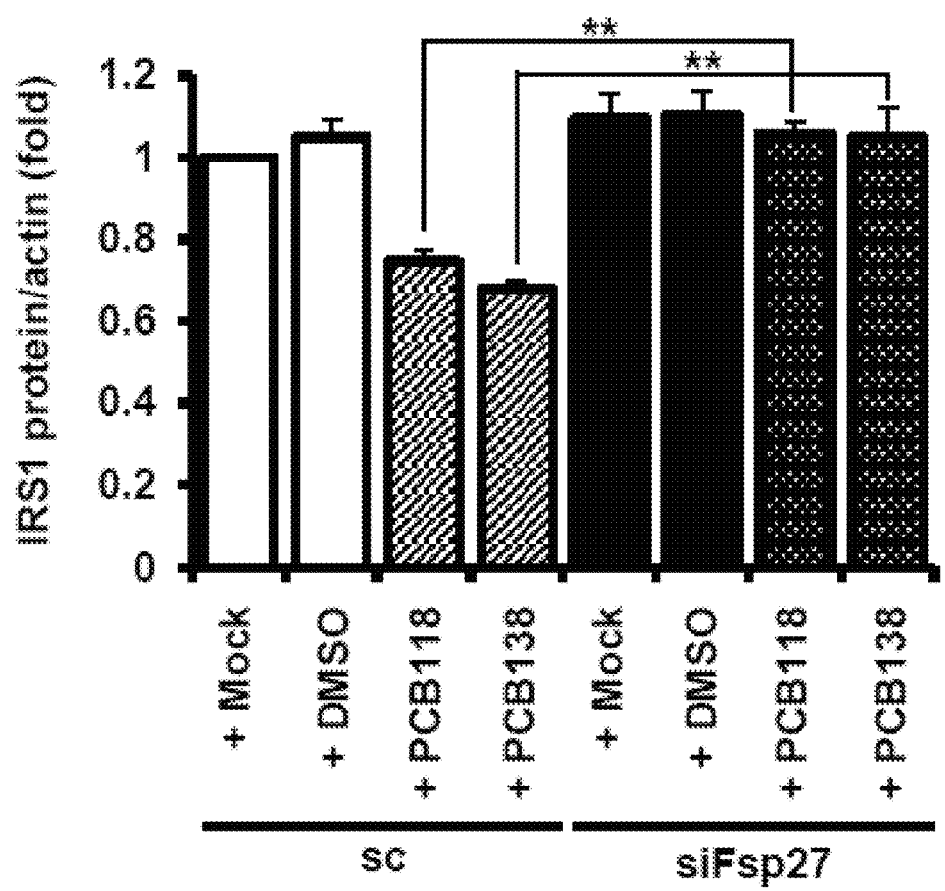

We further examined the molecular mechanism underlying PCB-induced large LD formation that mediates insulin resistance in vivo and in vitro. The protein level of IRS1, which is a critical element in insulin-signaling pathways, was markedly reduced in both PCB-administered mice (FIG. 5A) and 3T3-L1 adipocytes (FIG. 5B). However, PCBs did not alter mRNA levels of IRS1 (FIGS. 5A and 5B). We further determined whether Fsp27 plays a role in PCB-induced reduction of IRS1 protein. Importantly, siFsp27 reversed PCB-induced IRS1 reduction (FIG. 5C). These results indicate that Fsp27 mediates PCB-induced insulin resistance through IRS1 reduction.

Figure 6A:
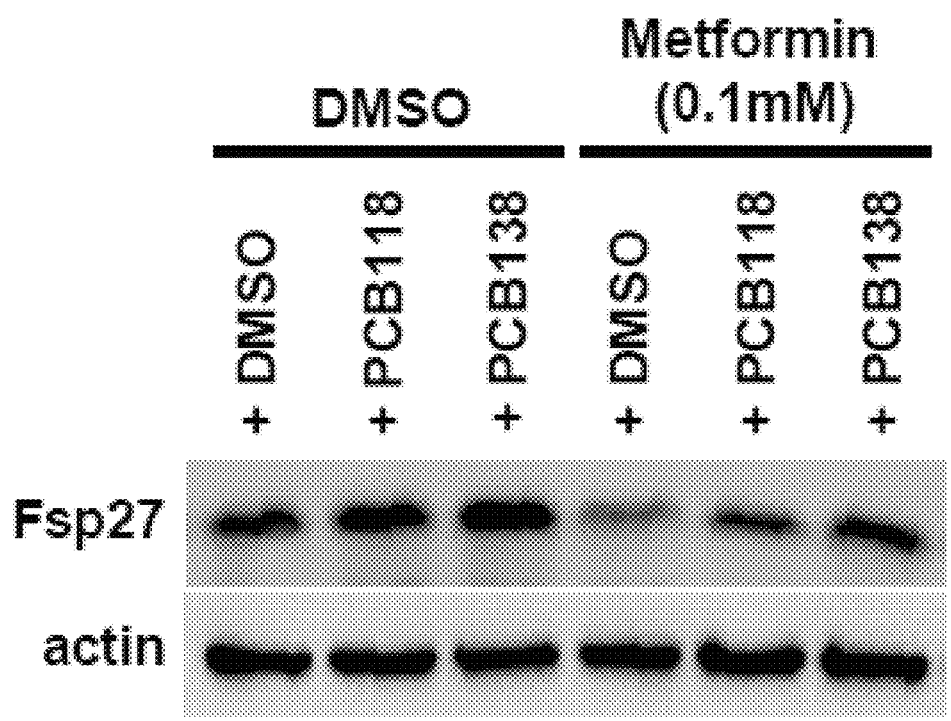
Figure 6C:
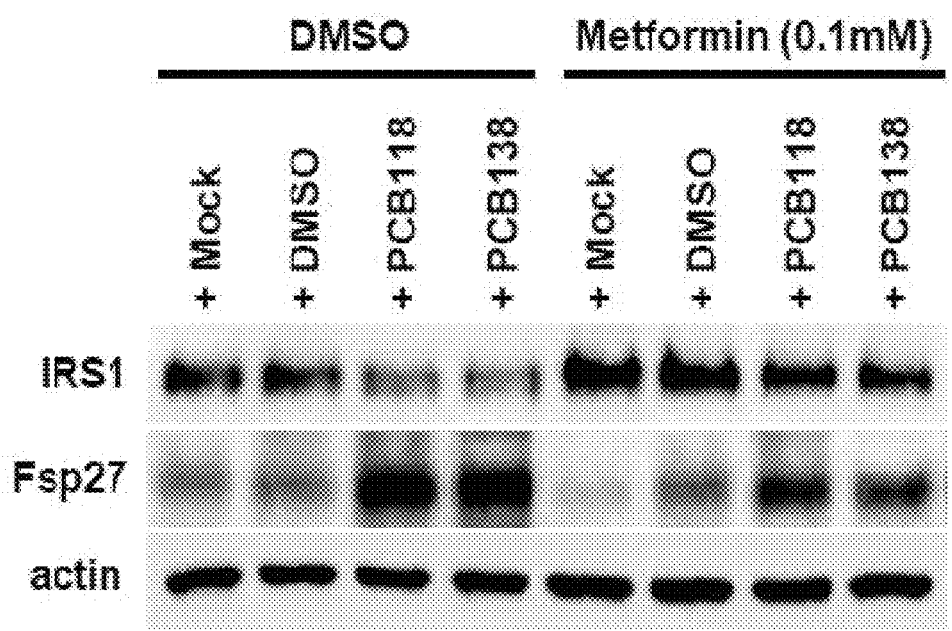
Figure 6D:
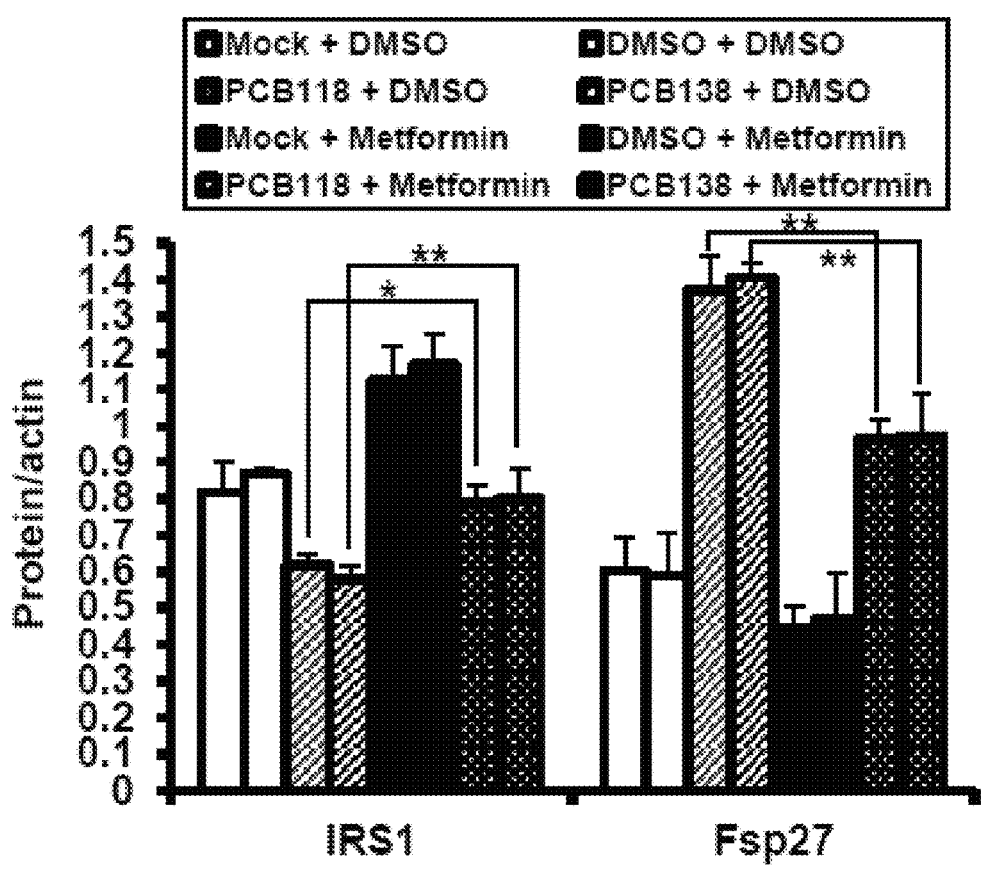
Figure 6E:
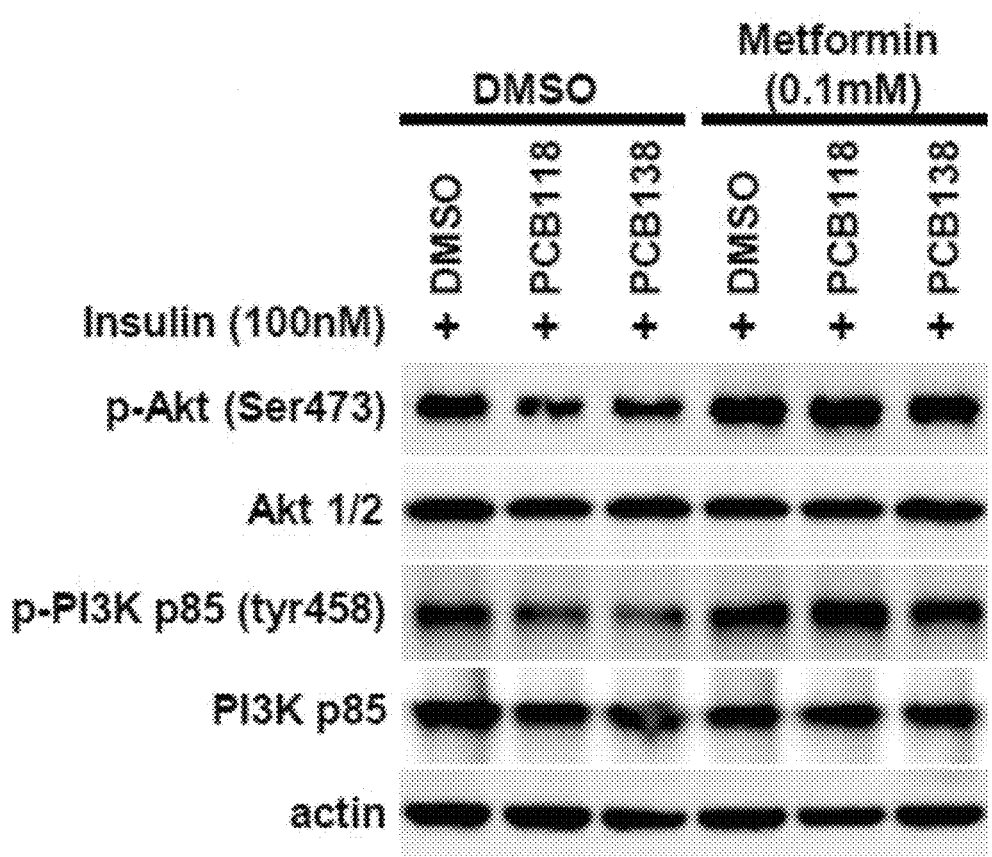

Metformin Reduces LD Size and Increases IRS1 Protein Level in PCB-Treated 3T3-L1 Adipocytes Through Downregulation of Fsp27 Protein We examined whether metformin, a representative insulin resistance-improving drug, alleviates PCB-induced insulin resistance through Fsp27. Metformin not only reduced the expression level of Fsp27, but reversed PCB-induced upregulation of Fsp27 expression (FIG. 6A). Phase contrast microscopy showed that metformin reversed PCB-induced LD enlargement (FIG. 6B). The reversal by metformin of Fsp27 upregulation was correlated with the reversal by metformin of IRS1 downregulation in adipocytes exposed to PCBs (FIG. 6C). Remarkably, metformin reversed the impairment by PCBs of the insulin-induced upregulation of p-Akt (Ser473) and p-PI3K p85 (Tyr458) (FIG. 6E). These findings indicate that metformin may improve PCB-induced insulin resistance through inhibition of LD enlargement via downregulation of Fsp27 protein.

Both Fsp27-Specific siRNA and Metformin Reverts the Accumulation of PCBs

To this end, we examined whether Fsp27-specific siRNA and metformin reverts accumulation of PCBs. Both Fsp27-specific siRNA and metformin reverted the accumulation of PCB-118 and PCB-138 in adipocytes.

Although the exemplary embodiments of the present disclosure have been described in detail with reference to the accompanying drawings, the present disclosure is not limited thereto and may be embodied in many different forms without departing from the technical concept of the present disclosure. Therefore, the exemplary embodiments of the present disclosure are provided for illustrative purposes only but not intended to limit the technical concept of the present disclosure. The scope of the technical concept of the present disclosure is not limited thereto. Therefore, it should be understood that the above-described exemplary embodiments are illustrative in all aspects and do not limit the present invention. The protective scope of the present disclosure should be construed based on the following claims, and all the technical concepts in the equivalent scope thereof should be construed as falling within the scope of the present disclosure.

SEQUENCE LISTING

<160> NUMBER OF SEQ ID NOS: 2

<210> SEQ ID NO 1

<211> LENGTH: 251
<212> TYPE: PRT
<213> ORGANISM: Artificial Sequence
<220> FEATURE:
<223> OTHER INFORMATION: Fsp27 protein sequence

<400> SEQUENCE: 1

Met Arg Asn Met Glu Ser Asn Ala Val Gln Leu Thr Arg Met Glu Tyr
1               5                   10                  15

Ala Met Lys Ser Leu Ser Leu Leu Tyr Pro Lys Ser Leu Ser Arg His
            20                  25                  30

Val Ser Val Arg Thr Ser Val Val Thr Gln Gln Leu Leu Ser Glu Pro
        35                  40                  45

Ser Pro Lys Ala Pro Arg Ala Arg Pro Cys Arg Val Ser Thr Ala Asp
    50                  55                  60

Arg Ser Val Arg Lys Gly Ile Met Ala Tyr Ser Leu Glu Asp Leu Leu
65                  70                  75                  80

Leu Lys Val Arg Asp Thr Leu Met Leu Ala Asp Lys Pro Phe Phe Leu
                85                  90                  95

Val Leu Glu Glu Asp Gly Thr Thr Val Glu Thr Glu Tyr Phe Gln
            100                 105                 110

Ala Leu Ala Gly Asp Thr Val Phe Met Val Leu Gln Lys Gly Gln Lys
        115                 120                 125

Trp Gln Pro Pro Ser Glu Gln Gly Thr Arg His Pro Leu Ser Leu Ser
    130                 135                 140

His Lys Pro Ala Lys Lys Ile Asp Val Ala Arg Val Thr Phe Asp Leu
145                 150                 155                 160

Tyr Lys Leu Asn Pro Gln Asp Phe Ile Gly Cys Leu Asn Val Lys Ala
                165                 170                 175

Thr Phe Tyr Asp Thr Tyr Ser Leu Ser Tyr Asp Leu His Cys Cys Gly
            180                 185                 190

Ala Lys Arg Ile Met Lys Glu Ala Phe Arg Trp Ala Leu Phe Ser Met
        195                 200                 205

Gln Ala Thr Gly His Val Leu Leu Gly Thr Ser Cys Tyr Leu Gln Gln
    210                 215                 220

Leu Leu Asp Ala Thr Glu Glu Gly Gln Pro Pro Lys Gly Lys Ala Ser
225                 230                 235                 240

Ser Leu Ile Pro Thr Cys Leu Lys Ile Leu Gln
                245                 250

<210> SEQ ID NO 2
<211> LENGTH: 239
<212> TYPE: PRT
<213> ORGANISM: Artificial Sequence
<220> FEATURE:
<223> OTHER INFORMATION: Fsp27 protein sequence

<400> SEQUENCE: 2

Met Asp Tyr Ala Met Lys Ser Leu Ser Leu Leu Tyr Pro Arg Ser Leu
1               5                   10                  15

Ser Arg His Val Ala Val Ser Thr Ala Val Val Thr Gln Gln Leu Val
            20                  25                  30

Ser Lys Pro Ser Arg Glu Thr Pro Arg Ala Arg Pro Cys Arg Val Ser
        35                  40                  45

Thr Ala Asp Arg Lys Val Arg Lys Gly Ile Met Ala His Ser Leu Glu
    50                  55                  60

Asp Leu Leu Asn Lys Val Gln Asp Ile Leu Lys Leu Lys Asp Lys Pro

|  |  |  |  |  |  |  |  |  |  |  |  |  |  |  |  |
|---|---|---|---|---|---|---|---|---|---|---|---|---|---|---|---|
| 65 |  |  |  |  | 70 |  |  |  |  | 75 |  |  |  |  | 80 |
| Phe | Ser | Leu | Val | Leu<br>85 | Glu | Glu | Asp | Gly | Thr<br>90 | Ile | Val | Glu | Thr | Glu<br>95 | Glu |
| Tyr | Phe | Gln | Ala<br>100 | Leu | Ala | Lys | Asp | Thr<br>105 | Met | Phe | Met | Val | Leu<br>110 | Leu | Lys |
| Gly | Gln | Lys<br>115 | Trp | Lys | Pro | Pro | Ser<br>120 | Glu | Gln | Arg | Lys | Lys<br>125 | Arg | Ala | Gln |
| Leu | Ala<br>130 | Leu | Ser | Gln | Lys | Pro<br>135 | Thr | Lys | Lys | Ile | Asp<br>140 | Val | Ala | Arg | Val |
| Thr<br>145 | Phe | Asp | Leu | Tyr | Lys<br>150 | Leu | Asn | Pro | Gln | Asp<br>155 | Phe | Ile | Gly | Cys | Leu<br>160 |
| Asn | Val | Lys | Ala | Thr<br>165 | Leu | Tyr | Asp | Thr | Tyr<br>170 | Ser | Leu | Ser | Tyr | Asp<br>175 | Leu |
| His | Cys | Tyr | Lys<br>180 | Ala | Lys | Arg | Ile | Val<br>185 | Lys | Glu | Met | Leu | Arg<br>190 | Trp | Thr |
| Leu | Phe | Ser<br>195 | Met | Gln | Ala | Thr | Gly<br>200 | His | Met | Leu | Leu | Gly<br>205 | Thr | Ser | Ser |
| Tyr | Met<br>210 | Gln | Gln | Phe | Leu | Asp<br>215 | Ala | Thr | Glu | Glu | Glu<br>220 | Gln | Pro | Ala | Lys |
| Ala<br>225 | Lys | Pro | Ser | Ser | Leu<br>230 | Leu | Pro | Ala | Cys | Leu<br>235 | Lys | Met | Leu | Gln |  |

What is claimed is:

1. A method for treating endocrine disrupting chemicals-induced diseases, the method comprising administrating Fsp27 protein-specific siRNA or a pharmaceutically acceptable salt thereof to patients requiring the siRNA or the salt,
   wherein the endocrine disrupting chemical is polychlorinated biphenyl; and
   the endocrine disrupting chemicals-induced diseases are one or more diseases selected from the group consisting of obesity, insulin resistance, and type II diabetes.

2. The method for treating endocrine disrupting chemicals-induced diseases of claim 1, wherein the sequence of the Fsp27 protein is SEQ ID NO: 1 or 2.

3. The method for treating endocrine disrupting chemicals-induced diseases of claim 1, wherein the Fsp27 protein-specific siRNA or the pharmaceutically acceptable salt thereof is administrated with an effective dose of 0.1 to 10 mg/Kg once.

4. The method for treating endocrine disrupting chemicals-induced diseases of claim 1, wherein the Fsp27 protein-specific siRNA or the pharmaceutically acceptable salt thereof is administrated 7 to 21 times per week.

5. The method for treating endocrine disrupting chemicals-induced diseases of claim 1, wherein the Fsp27 protein-specific siRNA or the pharmaceutically acceptable salt thereof is administrated parenterally.

6. The method for treating endocrine disrupting chemicals-induced diseases of claim 1, the method further comprising:
additionally administrating metformin or a pharmaceutically acceptable salt thereof.

7. The method for treating endocrine disrupting chemicals-induced diseases of claim 6, wherein the metformin or the pharmaceutically acceptable salt thereof is administrated orally or parenterally.

8. The method for treating endocrine disrupting chemicals-induced diseases of claim 6, wherein the metformin or the pharmaceutically acceptable salt thereof is administrated with an effective dose of 0.1 to 100 mg/Kg once.

9. The method for treating endocrine disrupting chemicals-induced diseases of claim 6, wherein the metformin or the pharmaceutically acceptable salt thereof is administrated 7 to 21 times per week.

10. The method for treating endocrine disrupting chemicals-induced diseases of claim 6, wherein the metformin or the pharmaceutically acceptable salt thereof is administrated together with the Fsp27 protein-specific siRNA or the pharmaceutically acceptable salt thereof.

11. A method for excreting endocrine disrupting chemicals, the method comprising adding Fsp27 protein-specific siRNA to tissues comprising the endocrine disrupting chemicals,
   wherein the endocrine disrupting chemical is polychlorinated biphenyl.

12. The method for excreting endocrine disrupting chemicals of claim 11, further comprising:
adding metformin or a pharmaceutically acceptable salt thereof.

* * * * *